US012662511B2

(12) United States Patent
Brown et al.

(10) Patent No.: US 12,662,511 B2
(45) Date of Patent: Jun. 23, 2026

(54) MOLECULAR TRANSPORT SYSTEM TO THE CENTRAL NERVOUS SYSTEM

(71) Applicant: SRI International, Menlo Park, CA (US)

(72) Inventors: Kathlynn C. Brown, Menlo Park, CA (US); Michael McGuire, Menlo Park, CA (US); Indu Venugopal, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 826 days.

(21) Appl. No.: 17/912,482

(22) PCT Filed: Mar. 18, 2021

(86) PCT No.: PCT/US2021/022979
§ 371 (c)(1),
(2) Date: Sep. 16, 2022

(87) PCT Pub. No.: WO2021/188802
PCT Pub. Date: Sep. 23, 2021

(65) Prior Publication Data
US 2023/0174580 A1 Jun. 8, 2023

Related U.S. Application Data

(60) Provisional application No. 62/991,465, filed on Mar. 18, 2020.

(51) Int. Cl.
*C07K 7/08* (2006.01)
*A61P 25/00* (2006.01)

(52) U.S. Cl.
CPC ............... *C07K 7/08* (2013.01); *A61P 25/00* (2018.01)

(58) Field of Classification Search
CPC ........... C07K 7/08; A61P 25/00; A61K 47/64; A61K 38/00
See application file for complete search history.

(56) References Cited

U.S. PATENT DOCUMENTS

| | | | |
|---|---|---|---|
| 11,738,089 B2 | 8/2023 | Brown et al. | |
| 11,738,098 B2 | 8/2023 | Yang et al. | |
| 11,965,004 B2 | 4/2024 | Brown et al. | |
| 2006/0280724 A1 | 12/2006 | Ferguson et al. | |
| 2010/0247457 A1 * | 9/2010 | Anton ................. | A61K 8/0241 |
| | | | 530/324 |
| 2010/0247589 A1 | 9/2010 | Fahnestock et al. | |
| 2012/0227131 A1 | 9/2012 | Abad et al. | |
| 2013/0121915 A1 | 5/2013 | Paas et al. | |
| 2017/0281752 A1 | 10/2017 | Brown et al. | |

FOREIGN PATENT DOCUMENTS

| | | |
|---|---|---|
| JP | 2015-502369 B2 | 1/2015 |
| WO | 2005049806 A2 | 6/2005 |
| WO | 2006086870 A1 | 8/2006 |
| WO | 2010117753 A3 | 10/2010 |
| WO | 2013096318 A2 | 6/2013 |
| WO | 2021066931 A1 | 4/2021 |

OTHER PUBLICATIONS

Shao (Journal of Controlled Release, 2010, 147, 118-126) (Year: 2010).*
Balci (Journal of Polymer Research, 2018, 25:104, 1-12) (Year: 2018).*
Brown, "Pettidic Tumor Targeting Agents the Road from Phage Display Peptide Selections to Clinical Applications", Currnet Pharmaceutical Design, 16(9): 1040-1054 (Mar. 1, 2010).
Bruno, et al. Bruno, Ther. Deliv. Nov. 2013; 4(11): 1443-1467.
Drazic, et al., Biochimica et Biophysica Acta (BBA)—Proteins and Proteomics, vol. 1864, Issue 10, Oct. 2016, pp. 1372-1401.
Kuang et al., "The design of peptide-amphiphiles as funcional ligands for liposomal anticancer drug and gene delivery", Advanced Drug Delivery Reviews, 110-111 (2017) 80-101.
McGuire et al., "Identification and Characterization of a Suite of Tumor Traeting Peptides for Non-Small Cell Lung Cancer", Scientific Reports, 4(1): 1-11, (Mar. 27, 2014).
Singh et al., "Dimerization of a Phage-Display Selected Peptide for Imaging of αvβ—Integrin: Two Approaches to the Multivalent Effect", Theranostics, 4(7): 745-760 (May 15, 2014).
Umlauf et al., "Identification of a Novel Lysosomal Trafficking Peptide Using Phage Display Biopanning Coupled with Endocytic Selection Pressure", Bioconjugate Chem, 25:1829-1837 (Sep. 4, 2014).
Umlauf et al., "Modular Three-components Delivery System Facilitates HLA Class I Antigen Presentation and CD8+ T-cell Activiation Against Tumors", Molecular Therapy, 23(6): 1092-1102 (Jun. 2015).
International Search Report and Written Opinion were mailed on Aug. 25, 2021 for Application No. PCT/US2021/022979, which was filed on Mar. 18, 2021 (Applicant: SRI International) (17 pages).
U.S. Appl. No. 62/991,465, filed Mar. 18, 2020, SRI International.
PCT/US2021/022979 (WO 2021/188802 A1), Mar. 18, 2021 (Sep. 23, 2021), SRI International.
Urich Eduard et al: "Cargo Delivery into the Brain by in vivo identified Transport Peptides", Scientific Reports, vol. 5, No. 1, Sep. 28, 2015.

* cited by examiner

*Primary Examiner* — Sudhakar Katakam
(74) *Attorney, Agent, or Firm* — Dicke, Billig & Czaja, PLLC

(57) ABSTRACT

Disclosed herein are MTS peptides or targeting peptides. Disclosed are MTS peptides comprising the amino acid sequence of any one of SEQ ID NOs: 1-12. Disclosed are compositions comprising a peptide, wherein the peptide comprises a first MTS peptide conjugated to a cargo. Also disclosed are methods of using the MTS peptides. For example, disclosed are methods of transporting cargo to the CNS comprising administering one or more of the disclosed compositions to a subject in need thereof, wherein the peptide conjugated to cargo enters the CNS.

14 Claims, 37 Drawing Sheets

Specification includes a Sequence Listing.

FIG. 11

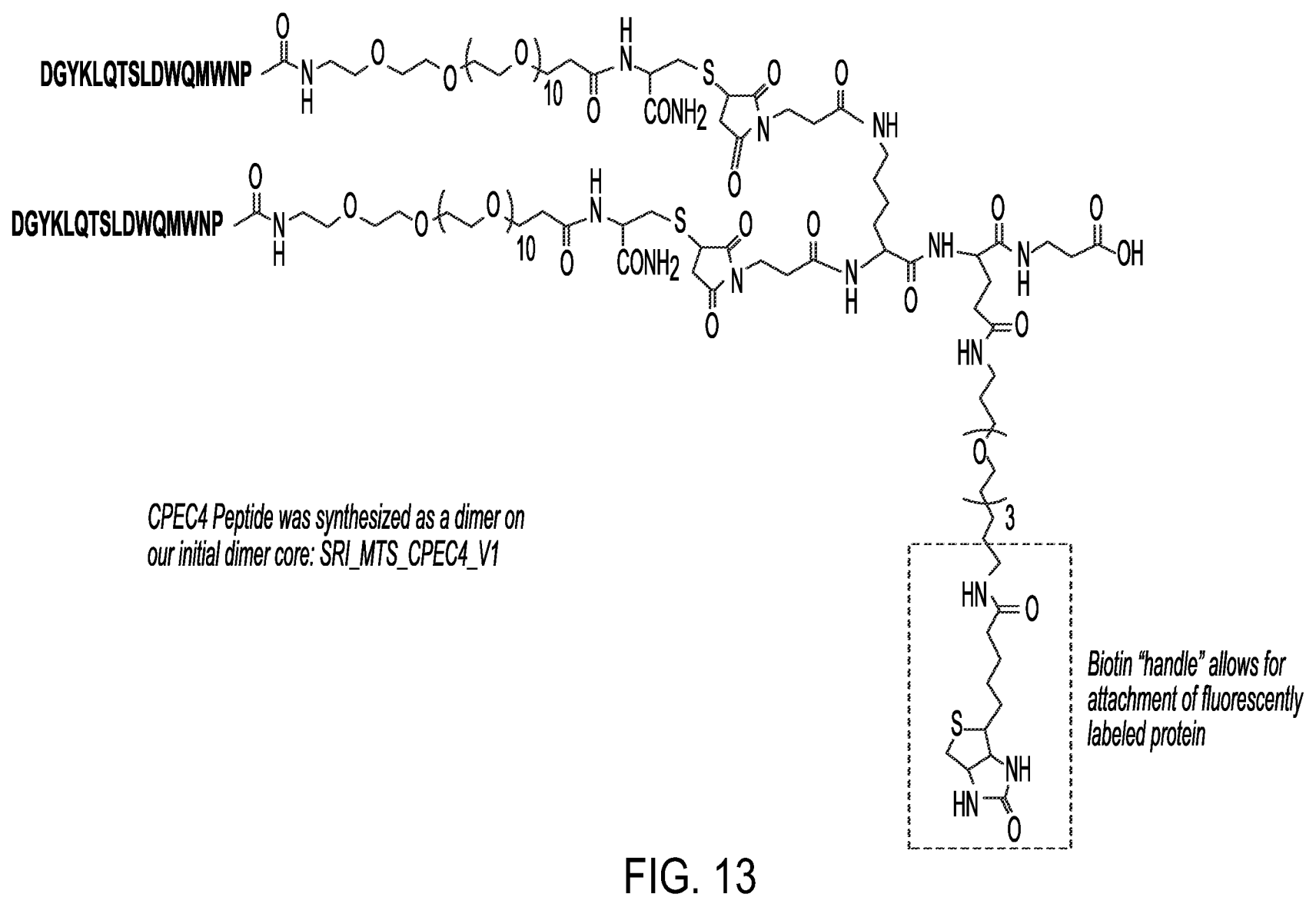

Biotin "handle" allows for attachment of fluorescently labeled protein

CPEC4 Peptide was synthesized as a dimer on our initial dimer core: SRI_MTS_CPEC4_V1

FIG. 13

Rat Z310 Transformed Cells

| Phage Clone | Input (Top Well) | Output (Bottom Well) | Output/Input Ratio | CPEC4/Empty Ratio |
|---|---|---|---|---|
| CPEC_4 | $1.6 \times 10^{10}$ | $1.9 \times 10^7$ | $1.2 \times 10^{-3}$ | 208 |
| Empty | $2.9 \times 10^{10}$ | $1.6 \times 10^5$ | $5.6 \times 10^{-6}$ | |

| Tracking Molecule | Arbitrary Fluorescence Units | | Ratio Output/Input | CPEC4/Dextran Ratio |
|---|---|---|---|---|
| | Top Well | Bottom Well | | |
| Dextran-647 | $3.6 \times 10^7$ | $8.3 \times 10^4$ | $2.3 \times 10^{-3}$ | 47 |
| MTS_CPEC4_V1_SA488 | $1.2 \times 10^7$ | $1.3 \times 10^6$ | $1.1 \times 10^{-1}$ | |

MTS_CPEC4_V2: Ac-DAYKLQTSLDWQMWNP-PEG11-NH2

PBS, pH 7.4

R
MTS Structure
on Core

MTS = Peptide Sequences Identified in the Patent Application

R'

This is our current modification

There are other options such as alkyl amines, alkyl carboxylic acids, PEG, lipidation, D-amino acids, or glycosylation

FIG. 28 continued

Monomer-Dimer

Dimer-Monomer

Peptide 1

Peptide 1

Peptide 2

Monomer-Monomer

Peptide 1

Peptide 2

FIG. 29 continued

R₁ Substituents for Peptide-Peptide Chimeras

R₁ can be any combination of these on either peptide

R₂ Substituents are shown below

FIG. 29 continued

Chemically Reactive Moieties for Conjugation to Cargo

R2 can be any combination of these on either peptide

MOLECULAR TRANSPORT SYSTEM TO THE CENTRAL NERVOUS SYSTEM

CROSS-REFERENCE TO RELATED APPLICATIONS

This application is a national stage application under 35 U.S.C. § 371 of International Application No. PCT/US2021/022979, filed on Mar. 18, 2021, which claims the benefit of U.S. Provisional Patent Application No. 62/991,465 filed on Mar. 18, 2020. The content of these earlier filed applications is hereby incorporated herein by reference in their entirety.

REFERENCE TO SEQUENCE LISTING

The Sequence Listing submitted Sep. 16, 2022 as a text file named "37794_0096U2_Sequence_Listing.txt," created on Sep. 16, 2022, and having a size of 3,476, bytes is hereby incorporated by reference pursuant to 37 C.F.R. § 1.52(e)(5).

BACKGROUND

Access to the Central Nervous System (CNS) is the bottleneck in neurotherapeutic development. This is due to the blood brain barrier (BBB) which is a set of specialized and highly selective cellular barriers that protects the Central Nervous System (CNS). While necessary under normal physiology, the BBB prevents entry of many chemical entities such as neurotherapeutics into the brain. As a result, less than 5% of small molecule drugs cross the BBB. Furthermore, newer biologic therapies such as antibodies and gene therapies are essentially excluded from the CNS due to the BBB. Despite the discovery of the BBB over 100 years ago, no general solution for delivery to the CNS has been created. For this reason, many CNS disorders have no treatment options.

Currently, there are several approaches that others have employed to delivery to the CNS. One approach is using BBB permeable compounds. The problems with using BBB permeable compounds are that they tend to have poor biodistribution properties and off-target effects (as they often tend to be highly lipid soluble). There are also few BBB permeable compounds as less than 5% of small molecules penetrate the BBB. BBB permeable agents also have limited indications.

Another approach to access the CNS is by direct injection into the spinal cord or brain. This method is invasive and there is a risk of structural damage to surrounding tissue as well as increased risk of infection Disruption of the BBB is another method used. This method allows mass transport of compounds, cells, and pathogens into the CNS. This method can cause structural damage as well as neuronal dysfunction.

Intranasal delivery has also been used. This method is limited to lipophilic, small molecule drugs. Intranasal delivery has been shown to have poor distribution through the CNS. Further, intranasal delivery has variable absorption between doses and patients.

Receptor-mediated delivery (Trojan horse) methods have also been employed. This method lacks generality as it is often only effective for a single cargo. The receptors can be expressed in multiple tissues leading to poor uptake in the CNS and toxicity. Further, most receptor-mediated delivery have no cell specificity once delivered past the BBB and distribution throughout the CNS is inconsistent.

There are no known choroid plexus transporting agents or alternative methods to transport cargo across the blood cerebral spinal fluid barrier, offering a unique development opportunity to impact transport of drugs and macromolecules into the CNS. Thus, disclosed herein are compositions and methods for targeting the CNS.

BRIEF SUMMARY

Described herein is a selection platform that exploits the biology of the choroid plexus to identify molecular transport system (MTS) peptides that can carry a variety of functional cargos into the cerebral spinal fluid where the cargo can be distributed to cells of the CNS. Disclosed herein are MTS peptides for CNS delivery of a cargo (e.g. biologically active cargo) to the brain.

Disclosed herein are MTS peptides or targeting peptides. Disclosed are MTS peptides comprising the amino acid sequence of any one of SEQ ID NOs: 1-12.

Also disclosed are peptides comprising a MTS peptide conjugated to a cargo.

Disclosed are compositions comprising a peptide, wherein the peptide comprises a first MTS peptide conjugated to a cargo. Disclosed are compositions comprising a peptide, wherein the polypeptide comprises a first MTS peptide conjugated to a cargo, wherein the first MTS peptide comprises the amino acid sequence of any one of SEQ ID NOs: 1-12.

Disclosed are methods of transporting cargo to the CNS comprising administering one or more of the disclosed compositions to a subject in need thereof, wherein the peptide conjugated to cargo enters the CNS. In some aspects, the peptide conjugated to cargo enters the choroid plexus.

Disclosed are methods of treating a CNS disorder or injury comprising administering one or more of the disclosed peptides or compositions to a subject in need thereof, wherein the cargo is a CNS disorder or injury therapeutic.

Disclosed are methods of imaging the CNS comprising administering one or more of the disclosed peptides or compositions to a subject in need thereof, wherein the cargo is an imaging agent.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 11 shows transwell selections on human primary choroid plexus epithelial cells.

FIG. 13 shows a dimer CPEC4 peptide.

FIG. 15 shows that a CPEC4 phage clone and MTS_CPEC4_V1 are transported through rat choroid plexus cells in an in vitro system. CPEC4 phage clone is a phage that displays the CPEC4 peptide (SEQ ID NO:2). MTS_CPEC4_V1 is the synthetic peptide of SEQ ID NO: 2.

Figure 19:
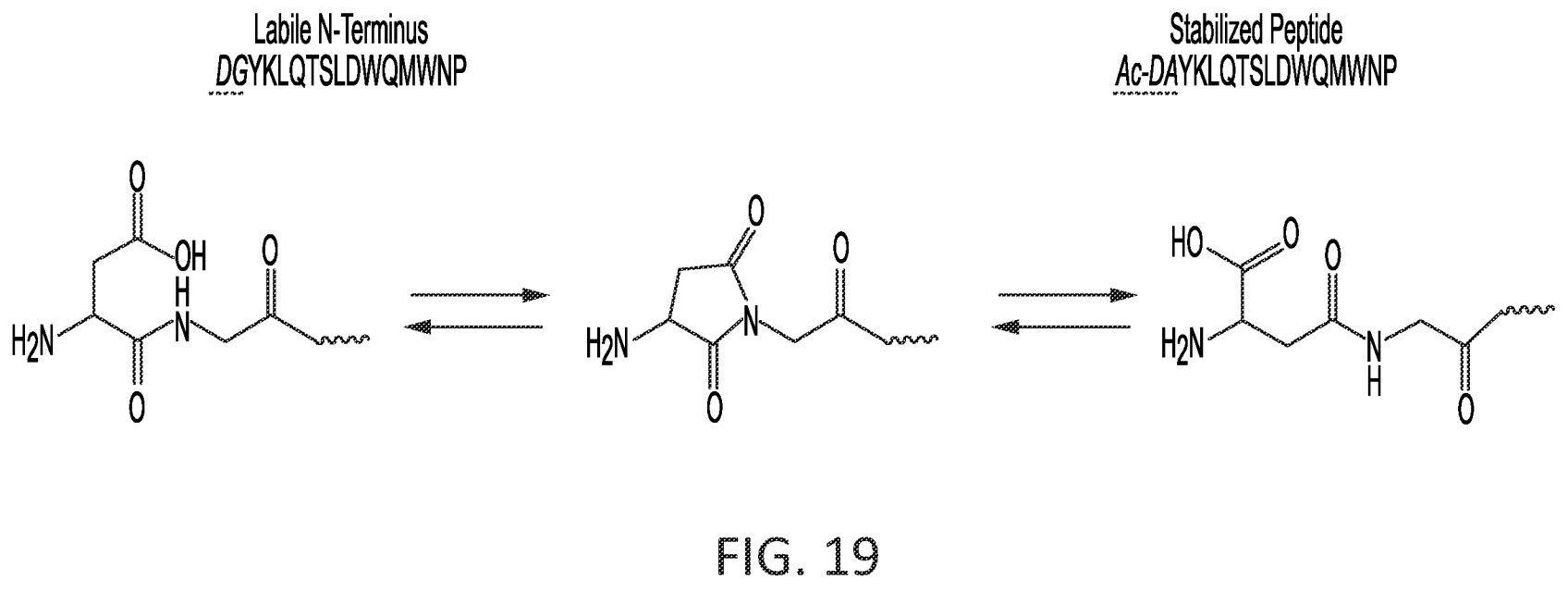

FIG. 19 shows the difference in MTS_CPEC4 before and after stabilization. MTS-CPEC4 comprises an MTS peptide having the sequence of DGYKLQTSLDWQMWNP (SEQ ID NO: 2).

FIG. 20 shows the synthesis of MTS_CPEC4_V2 using an isoacyl Thr-Ser dipeptide. MTS_CPEC4_V2 comprises an MTS peptide having the sequence of DAYKLQT-SLDWQMWNP (SEQ ID NO:1).

DETAILED DESCRIPTION

Figure 1:
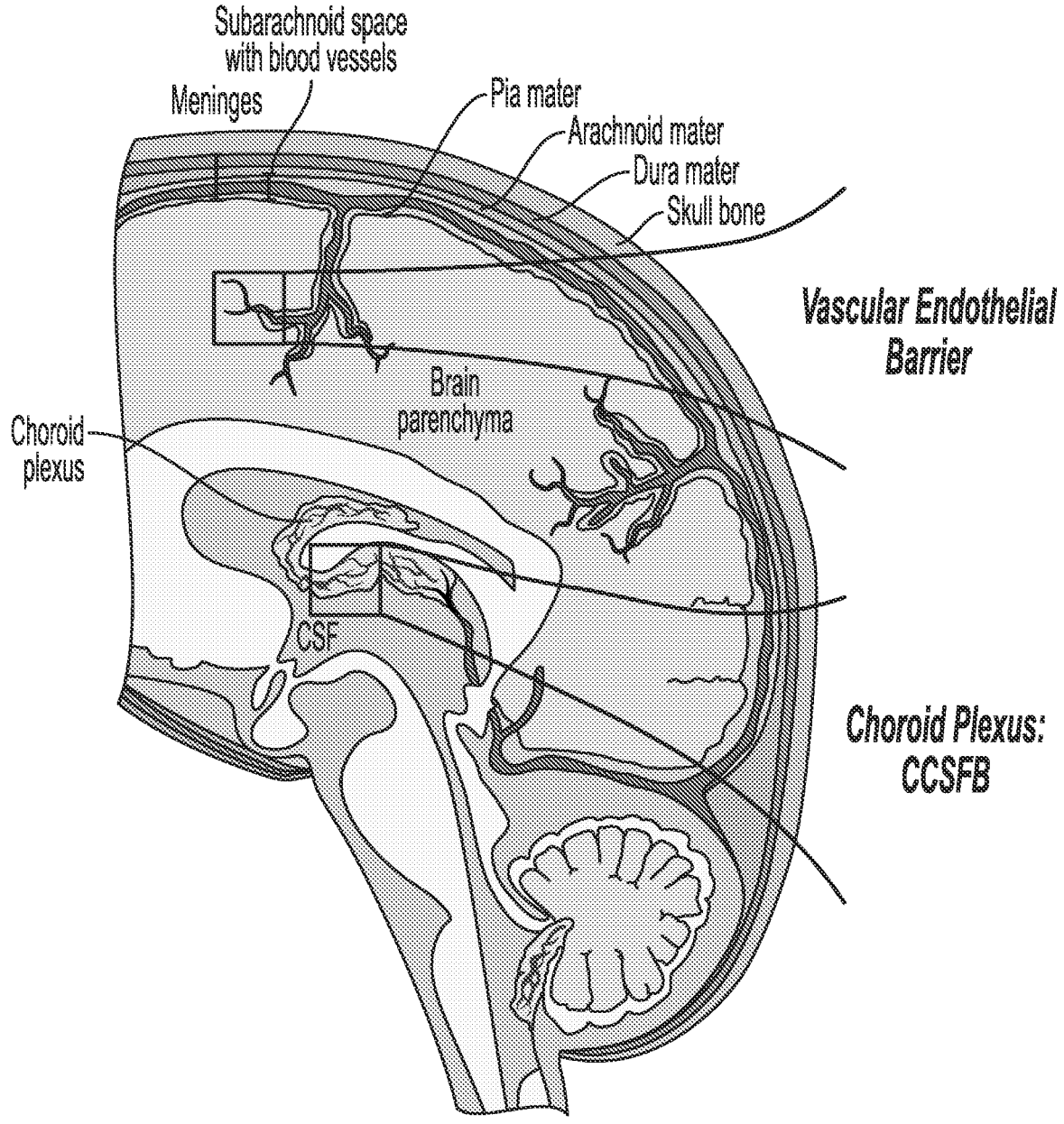
FIG. 1 shows a schematic of the brain with the Vascular Endothelial Barrier (usually referred to as the Blood Brain Barrier (BBB)) as well as the Choroid Plexus. CSF=cerebral spinal fluid: CCSFB=choroid cerebrospinal fluid barrier.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of the peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C: D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C: D, E, and F; and the example combination A-D. This concept applies to all aspects of this application including, but not limited to, steps in methods of making and using the disclosed compositions.

Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a peptide" includes a plurality of such peptides, reference to "the composition" is a reference to one or more compositions and equivalents thereof known to those skilled in the art, and so forth.

As used herein, "treat" is meant to mean administer a composition of the invention to a subject, such as a human or other mammal (for example, an animal model), that has a disease or condition, in order to prevent or delay a worsening of the effects of the disease or condition, or to partially or fully reverse the effects of the disease or condition. In some aspects, the disease or condition can be a CNS associated disease or condition or a CNS disorder or injury. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of one or more of the disclosed compositions to a subject.

As used herein, "prevent" is meant to mean minimize the chance that a subject who has an increased susceptibility for developing a disease, disorder or condition will develop the disease, disorder or condition.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and new born subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment prior to the administering step. In some aspects, patient and subject can be used interchangeably.

As used herein, the term "amino acid sequence" refers to a list of abbreviations, letters, characters or words representing amino acid residues. The amino acid abbreviations used herein are conventional one letter codes for the amino acids and are expressed as follows: A, alanine: C, cysteine:

D aspartic acid: E, glutamic acid: F, phenylalanine: G, glycine: H histidine; I isoleucine: K, lysine: L, leucine: M, methionine: N, asparagine: P, proline: Q, glutamine: R, arginine: S, serine: T, threonine: V, valine: W, tryptophan: Y, tyrosine.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (*See Proteins—Structure and Molecular Properties* 2nd Ed., T. E. Creighton, W.H. Freeman and Company, New York (1993): *Posttranslational Covalent Modification of Proteins*, B. C. Johnson, Ed., Academic Press, New York, pp. 1-12 (1983)).

The phrase "nucleic acid sequence" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acid sequences of the invention can also include nucleotide analogs (e.g., BrdU), and non-phosphodiester internucleoside linkages (e.g., peptide nucleic acid (PNA) or thiodiester linkages). In particular, nucleic acid sequences can include, without limitation, DNA, RNA, cDNA, gDNA, ssDNA, dsDNA or any combination thereof.

As used herein, "effective amount" of a composition is meant to mean a sufficient amount of the composition to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

As used herein, "selectively binds" is meant that a nucleic acid sequence (e.g. cargo) or MTS recognizes and physically interacts with its target (for example, a specific cell type) and does not significantly recognize and interact with other targets.

The term "percent (%) homology" is used interchangeably herein with the term "percent (%) identity" and refers to the level of nucleic acid or amino acid sequence identity when aligned with a wild type sequence or sequence of interest using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., any of the MTS sequences, as described herein. Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997. Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62matrix. (See, e.g., Altschul, S. F., et al., Nucleic Acids Res.25:3389-3402, 1997.) A preferred alignment of selected sequences in order to determine "% identity" between two or more sequences, is performed using for example, the CLUSTAL-W program in Mac Vector version 13.0.7, operated with default parameters, including an open gap penalty of 10.0, an extended gap penalty of 0.1, and a BLOSUM 30 similarity matrix.

Substitutions, deletions, insertions or any combination thereof may be used to arrive at a final derivative, variant, or analog. Generally, these changes are done on a few nucleotides to minimize the alteration of the molecule. However, larger changes may be tolerated in certain circumstances.

Generally, the nucleotide identity between individual variant sequences can be at least 90%, 91%, 92%, 93%, 94%, 95%, 96%, 97%, 98%, 99%, or 100%. Thus, a "variant sequence" can be one with the specified identity to the parent or reference sequence (e.g. wild-type sequence) of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent sequence. For example, a "variant sequence" can be a sequence that contains 1, 2, or 3, 4 nucleotide base changes as compared to the parent or reference sequence of the invention, and shares or improves biological function, specificity and/or activity of the parent sequence. Thus, a "variant sequence" can be one with the specified identity to the parent sequence of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent sequence. The variant sequence can also share at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of a reference sequence (e.g. a MTS sequence).

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Peptides

A peptide that can provide molecular transport or can target a specific location or site can be called a MTS peptide. A MTS peptide is an amino acid sequence that is known as a molecular transport system because it targets a specific location or site and thus, it can transport a cargo to the specific location or site. In some aspects, the MTS peptides disclosed herein target the CNS.

Disclosed herein are MTS peptides or targeting peptides. Disclosed are MTS peptides comprising the amino acid sequence of any of the sequences set forth in SEQ ID NOs: 1-10 as shown in Table 1. In some aspects an MTS peptide consists of an amino acid sequence responsible for molecular transport or targeting to a specific location or site. For example, in some aspects, the disclosed MTS peptides consist of the amino acid sequence of any of the sequences set forth in SEQ ID NOs: 1-10 as shown in Table 1.

TABLE 1

Example MTS peptides

| SEQ ID NO | Peptide sequence | Alternate names for the sequence |
|---|---|---|
| SEQ ID NO: 1 | DAYKLQTSLDWQMWNP | CPEC4DA<br>CPEC4_V2<br>CPEC4_V2-1 (monomeric)<br>CPEC4_V2-2 (dimeric)<br>MTS1_V2-1(monomeric)<br>MTS1_V2-2 (dimeric) |
| SEQ ID NO: 2 | DGYKLQTSLDWQMWNP | CPEC4_V1<br>CPEC4<br>MTS1_V1-1 (monomeric)<br>MTS1_V1-2 (dimeric) |
| SEQ ID NO: 3 | NQEYQHHKIKVRPSHQ | |
| SEQ ID NO: 4 | FPSWTSKNQQWTNQRQ | MTS_Z310-2<br>MTS2_V1-1 (monomeric)<br>MTS2_V1-2 (dimeric) |
| SEQ ID NO: 5 | AHMSQKRLPHQVHQHQ | |
| SEQ ID NO: 6 | AGNKYEYTMHQKHNK | |
| SEQ ID NO: 7 | SKETYSMNAQRQHERS | MTS_Z310-5<br>MTS3_V1-1 (monomeric)<br>MTS3_V1-2 (dimeric) |
| SEQ ID NO: 8 | HRYDADRHHSFTPQYH | |
| SEQ ID NO: 9 | NEEMHQAQRHHVQW | |
| SEQ ID NO: 10 | ALEPWGYKQVIKMAPN | |

In some aspects, the one or more MTS peptides have a sequence identity of at least 90, 91, 92, 93, 94, 95, 96, 97, 98, or 99% identity with any of the sequences set forth in SEQ ID NOs: 1-10. In some aspects, the one or more MTS peptides have a sequence identity of at least 90, 91, 92, 93, 94, 95, 96, 97, 98, or 99% identity with any of the MTS peptides disclosed herein. In some aspects, the one or more MTS peptides have 100% identity in the active portion of the peptide, wherein is the portion that retains its ability to cross from bloodinto the CSF. Thus, in some aspects, the at least 90, 91, 92, 93, 94, 95, 96, 97, 98, or 99% identity with any of the MTS peptides occurs outside of the active portion.

In some aspects, MTS peptides can be modified. In some aspects, modifying an MTS peptide comprises optimizing the peptide or stabilizing the peptide.

In some aspects, MTS peptides can be stabilized so that the MTS peptide remains intact (e.g. does not degrade)

during synthesis and/or storage. In some aspects, an MTS peptide comprising the sequence DGYKLQT-SLDWQMWNP (SEQ ID NO:2) can be stabilized by changing the glycine at the second amino acid position to alanine as in DAYKLQTSLDWQMWNP (SEQ ID NO: 1) and can be further optimized with an N-terminal acetyl protecting group. In some aspects, the aspartic acid and glycine dipeptide (the DG of SEQ ID NO:2) is able to form a cyclic intermediate (see FIG. 19). A cyclic intermediate can open back up to form the original MTS peptide or the non-natural amino acid therefore creating a less stable MTS peptide.

In some aspects, MTS peptides can be optimized. Optimized peptides can be obtained by applying modifications to the individual parental peptide sequences. These modifications can be used to identify the essential amino acids within the parental sequence that are required for crossing from the blood into the CSF. These modifications can be obtained by a combination of alanine scanning and truncations of the amino-terminal region and c-terminal region of the parental peptide. PEG11 can provide protection of the C-terminus of the MTS peptide, provide a spacer between the peptide and the cargo molecule attached through the cysteine at the C-terminus, and enhance solubility of the MTS peptide. Modification at the amino-terminus by acetylation (CH3CO—) and/or d-amino acids, such as d (Leu) can protect against degradation by peptidases in blood. There is not a uniform length of optimized peptide that can be applied to all MTS peptides and all changes can be tested to confirm the effect on peptide uptake and stability.

In some aspects, the MTS peptides disclosed herein can have an N-terminal protection group. In some aspects, the N-terminal protection group can be anything that prevents proteases from cleaving the amino acids from the N-terminus. In some aspects, the MTS peptides disclosed herein can be modified by acetylation on the N-terminus. In some aspects, the N-terminal protection group is an acetyl group. Thus, in some aspects, the MTS peptides disclosed herein can be acetylated. In some aspects, the N-terminal protection group can be, but is not limited to, PEGylation, Formyl, CH3-(CH)n-CO, Fluorophore, Fatty acid, alkyl amine, sulfonamide, or carbamamate. In some aspects, the MTS peptides disclosed herein can be chemically conjugated to a cargo, such as a nucleic acid sequence. In some aspects, the chemical conjugate can be polyethylene glycol (PEG). Thus, in some aspects, the MTS peptides disclosed herein can be pegylated. In some aspects, the number of PEG units can be 1, 2, 3, 4, 5, 6, 7, 8, 9, 10, 11, or more. In some aspects, the number of PEG units can be of sufficient length to separate the one or more MTS peptides from the cargo to prevent any steric interference between the one or more MTS peptides and the cargo. Thus, in some aspects, the MTS peptides disclosed herein can further comprise a linker. For example, the linker and the chemical conjugate can be used interchangeably. In some aspects, the linker is on the C-terminal end of the MTS peptide. For example, disclosed herein are compositions comprising a chemical conjugate or linker, wherein the chemical conjugate or linker is PEG and the PEG comprises eleven PEG units. In an aspect, the MTS peptides disclosed herein comprise one or more of the sequences set forth in SEQ ID NOs: 1-10, wherein SEQ ID NOs: 1-10 can be acetylated on the N-terminus and can be chemically conjugated to PEG; and the cargo, such as a nucleic acid sequence, can also be covalently attached to PEG. In some aspects, the N-terminal protection group can be an artificial amino acid, such as a D-amino acid.

In an aspect, the MTS peptides disclosed herein can be truncated. In some aspects, the MTS peptides disclosed herein are truncated to eliminate all amino acids except the active portion of the MTS peptide. In some aspects, the active portion of an MTS peptide can be used in the disclosed compositions and methods. In some aspects, the active portion can be determined using techniques well known in the art, for example Alanine scanning or truncation studies. The active portion of the MTS peptide is the portion that retains its ability to cross from the blood into the CSF. For example, SEQ ID NO: 7 can be truncated by up to four amino acids on the N-terminal end. In some aspects. SEQ ID NO:7 can be truncated by up to 8 amino acids on the C-terminal end. In some aspects, the amino acid sequence YSMNAQRQHERS (SEQ ID NO: 11) is the active portion of SEQ ID NO:7. In some aspects, the amino acid sequence YSMN (SEQ ID NO: 12) is the active portion of SEQ ID NO:7. Thus, in some aspects. SEQ ID NO:12 can be used as an MTS peptide.

In some aspects, disclosed are stabilized variants of MTS peptides disclosed herein.

Also disclosed are peptides comprising a MTS peptide conjugated to a cargo. In some aspects, two or more MTS peptides can be conjugated to a cargo.

Disclosed are peptides comprising a first MTS peptide conjugated to a cargo, wherein the first MTS peptide comprises the amino acid sequence of any of the sequences set forth in SEQ ID NOs: 1-12

In some aspects, a cargo molecule can be, but is not limited to, a nucleic acid sequence, protein, antibody, peptide, nanoparticle, dye, chemical compound, or small molecule. As described herein, the cargo is a nucleic acid sequence. In some aspects, the cargo can be an imaging agent, radionuclide, or detectable marker.

Disclosed are peptides comprising a first MTS peptide conjugated to a cargo and further comprising a second MTS peptide. For example, disclosed are peptides comprising a first MTS peptide conjugated to a cargo, wherein the first MTS peptide comprises the amino acid sequence of any of the sequences set forth in SEQ ID NOs: 1-12 and further comprising a second MTS peptide.

In some aspects, the second MTS peptide is the same as the first MTS peptide. In some aspects, the second MTS peptide is different from the first MTS peptide.

Attachment of the MTS to cargo can occur through maleimide chemistry, click chemistry, amide chemistry, and through hydrazones. The cargo can be attached using a cleavable or non-cleavable linker.

MTS dimers can be synthesized using linear peptide chemistry, such as FMOC (no maleimide group). The cargo can then be attached to the dimer through maleimide chemistry, click chemistry, amide chemistry, and through hydrazones.

Figure 28:
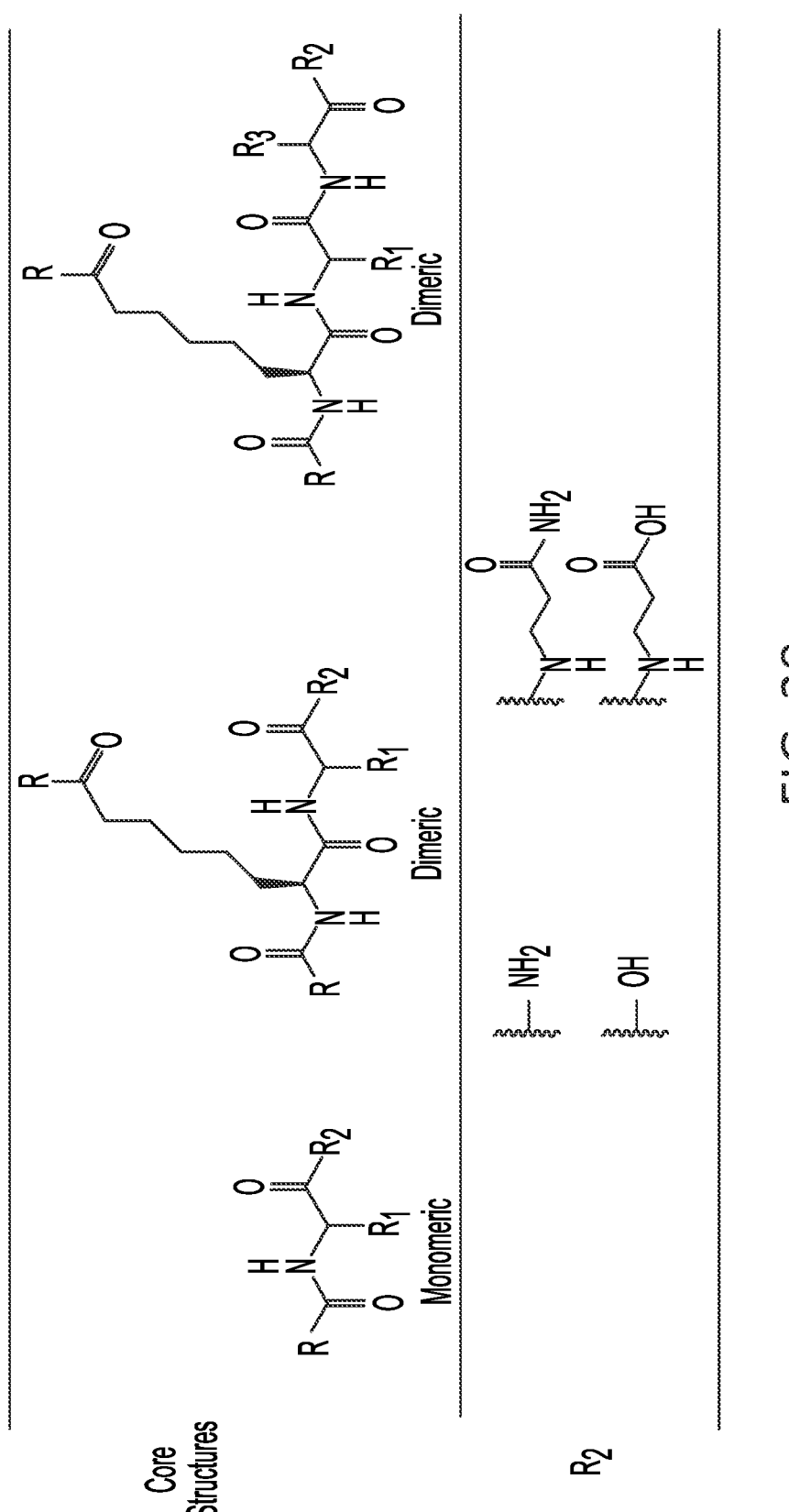
FIG. 28 shows how the dimer MTS can be conjugated together or conjugated to cargo.
Figure 29:
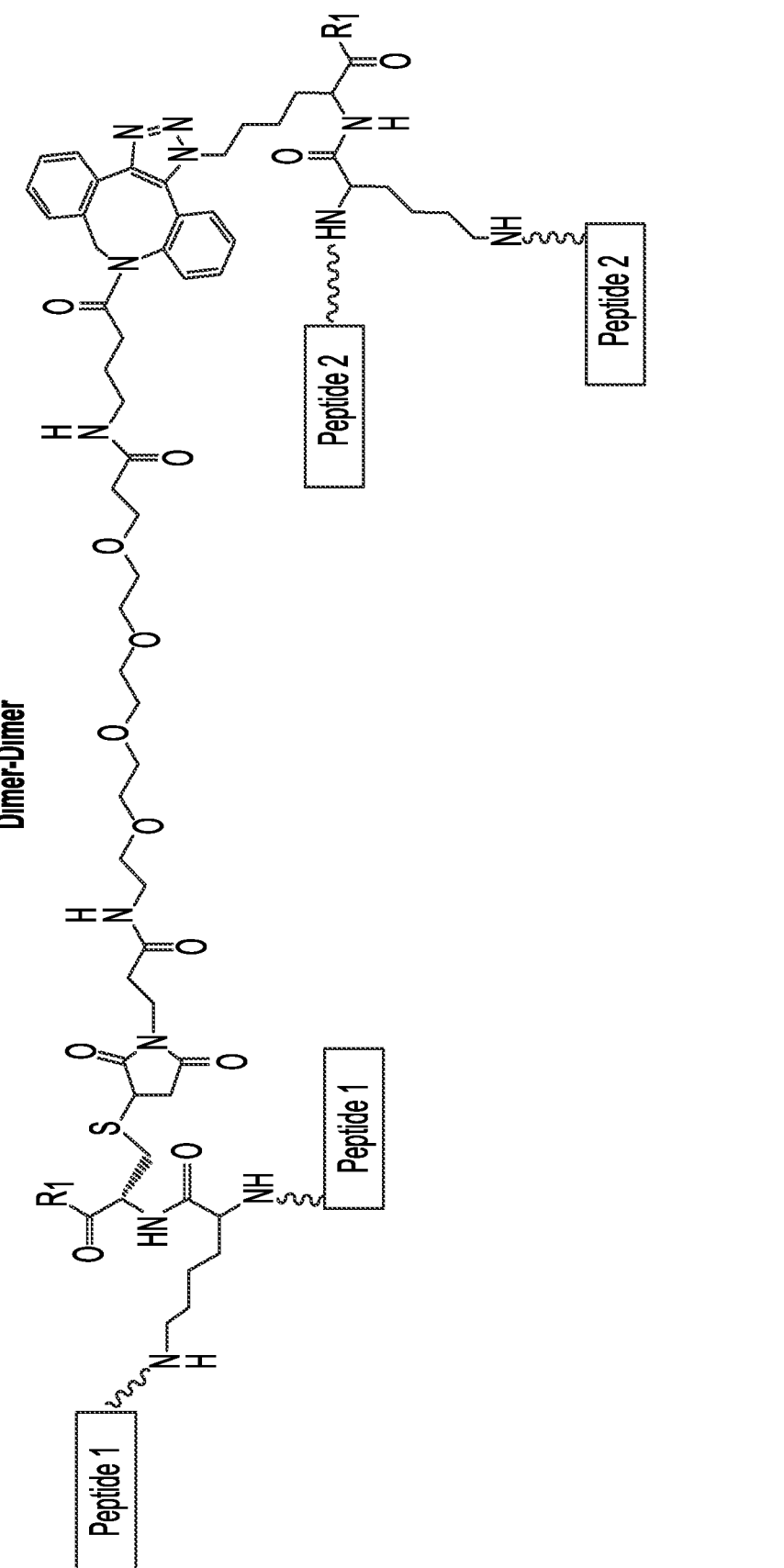
FIG. 29 shows examples of MTS chimeric molecules.
Figure 29:
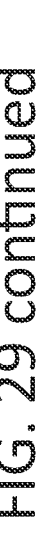

Examples of how conjugates are made are seen in FIG. 28 and FIG. 29.

C. Compositions

Disclosed are compositions comprising one of more of the disclosed peptides. In some aspects, disclosed are compositions comprising one or more of the MTS peptides disclosed herein. Also disclosed are compositions comprising a peptide, wherein the peptide comprises a first MTS peptide conjugated to a cargo.

For example, disclosed are compositions comprising a peptide, wherein the polypeptide comprises a first MTS peptide conjugated to a cargo, wherein the first MTS peptide comprises the amino acid sequence of any of the sequences set forth in SEQ ID NOs: 1-12.

1. Pharmaceutical Compositions

In some aspects, the disclosed compositions can be pharmaceutical compositions. For example, in some aspects, disclosed are pharmaceutical compositions comprising a composition comprising a nucleic acid sequence conjugated to one or more MTS peptides and a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC: Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro. Mack Publishing Company. Easton. PA 1995. Typically, an appropriate amount of pharmaceutically-acceptable salt is used in the formulation to render the formulation isotonic. Other examples of the pharmaceutically-acceptable carrier include, but are not limited to, saline. Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, or conjugate of the invention is not compromised. Pharmaceutical compositions may also include one or more active ingredients (in addition to the composition of the invention) such as antimicrobial agents, anti-inflammatory agents, anesthetics, and the like.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the fusion proteins. Thus, compositions can be prepared for parenteral administration that includes fusion proteins dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The pharmaceutical compositions described above can be formulated to include a therapeutically effective amount of a composition disclosed herein. In some aspects, therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to one or more autoimmune diseases or where the patient has a clinically determined predisposition or increased susceptibility (in some cases, a greatly increased susceptibility) to cancer.

The pharmaceutical compositions described herein can be administered to the subject (e.g., a human subject or human patient) in an amount sufficient to delay, reduce, or preferably prevent the onset of clinical disease. Accordingly, in some aspects, the subject is a human subject. In therapeutic applications, compositions are administered to a subject (e.g., a human subject) already with or diagnosed with a CNS disease or disorder in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effective amount includes amounts that provide a treatment in which the onset or progression of the cancer is delayed, hindered, or prevented, or the CNS disease or disorder or a symptom of the CNS disease or disorder is ameliorated. One or more of the symptoms can be less severe. Recovery can be accelerated in an individual who has been treated.

The total effective amount of the conjugates in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

D. Methods

Disclosed are methods of using one or more of the disclosed peptides (e.g. MTS peptides) or compositions.

Any of the peptides (e.g. MTS peptides) or compositions disclosed herein can be used in the methods disclosed herein. In some aspects of the disclosed methods, a MTS peptide conjugated to cargo can cross from the blood into the CNS.

1. Methods of Transporting Cargo

Disclosed are methods of transporting cargo to the CNS comprising administering one or more of the disclosed compositions to a subject in need thereof, wherein the MTS peptide conjugated to cargo enters the CNS. In some aspects, the MTS peptide conjugated to cargo enters the choroid plexus. In some aspects, the MTS peptide conjugated to cargo enters the cerebral spinal fluid (CSF). In some aspects, the CSF transports the MTS peptide conjugated to cargo throughout the CNS. In some aspects, the MTS peptide can be cleaved from the cargo resulting in the CSF transporting the cargo, separate from the MTS peptide, throughout the CNS.

In the disclosed methods, the cargo retains functional activity inside the CNS once it is delivered to the CNS.

In some aspects, administering is an intravenous administration. In some aspects, administering is intravenous (or intra-arterial), intramuscular, subcutaneous, intraperitoneal, transmucosal (e.g., intranasal), or transdermal (e.g., topical) administration. In some aspects, the administering can be via aerosol inhalation.

2. Methods of Treating

Disclosed are methods of treating a CNS disorder or injury comprising administering one or more of the disclosed peptides (e.g. MTS peptides) or compositions to a subject in need thereof, wherein the cargo is a CNS disorder or injury therapeutic.

In some aspects, a CNS disorder or injury can be, but is not limited to, Parkinson's, Alzheimer, Glioblastoma and other cancers that metastasize to the brain, Amyotrophic lateral sclerosis, Multiple sclerosis, and traumatic brain injury. Thus, in some aspects a CNS disorder or injury therapeutic can be, but is not limited to, an antibody, a gene therapy, a compound, a nucleic acid sequence or a peptide (or protein). In some aspects, specific examples of a CNS disorder or injury therapeutic can be, but are not limited to, an N-methyl D-aspartate (NMDA) antagonist, chemotherapeutic, glutamate antagonist, or immune modulator (e.g. immune suppressor or immune activator).

3. Methods of Imaging

Disclosed are methods of imaging the CNS comprising administering one or more of the disclosed peptides (e.g. MTS peptides) or compositions to a subject in need thereof, wherein the cargo is an imaging agent. As used herein, an imaging agent, imaging label, or imaging moiety (also detectable label, detectable moiety, or diagnostic moiety) refers to an atom, molecule or composition, wherein the presence of the atom, molecule or composition can be directly or indirectly measured.

In some aspects, an imaging agent can be, but is not limited to, a fluorescent dye, radioactive isotope, magnetic bead, metallic bead, colloidal particle, near-infrared dye, or an electron-dense reagent. Thus, detectable moieties can be, but are not limited to, fluorescent moieties, radioactive moieties, or electronic moieties. In some aspects, the imaging agent comprises two portions, wherein portion one comprises a disease specific peptide, nucleic acid, or compound conjugated to portion two, wherein portion two comprises a fluorescent dye, radioactive isotope, magnetic bead, metallic bead, colloidal particle, near-infrared dye, or an electron-dense reagent. In some aspects, portion one of the imaging agent binds to a disease specific indicator in the CNS and portion two of the imaging agent allows for detection or visualization of the imaging agent. In some aspects, the disease specific peptide, nucleic acid, or compound can bind to a protein or nucleic acid in the CNS indicative of a specific disease, such as, but not limited to Parkinson's, Alzheimer, Glioblastoma and other cancers that metastasize to the brain, Amyotrophic lateral sclerosis, Multiple sclerosis, and traumatic brain injury. The binding of a disease specific peptide, nucleic acid, or compound to a protein or nucleic acid in the CNS indicative of a specific disease can be detected or visualized by portion two of the imaging agent.

The disclosed methods of imaging the CNS can allow for the CNS to be monitored for the presence of disease or disease progression. For example, once the presence of a disease or disease progression is detected, a second MTS peptide conjugated to a cargo can be administered to the subject, wherein the cargo is a therapeutic. In some aspects, if the first peptide comprises a MTS peptide conjugated to a cargo, wherein the cargo is an imaging agent that identifies the presence of a glioblastoma in the CNS, then the second peptide can comprise a MTS peptide conjugated to a cargo, wherein the cargo is a gliobastoma specific therapeutic.

Also disclosed are methods of imaging the CNS comprising administering a peptide comprising one or more of the disclosed MTS peptides conjugated to a first cargo and a second cargo, wherein the first cargo is an imaging agent and the second cargo is a CNS disorder or injury therapeutic. Thus, in some aspects, the CNS can be imaged and if the presence of disease or disease progression is detected, the CNS disorder or injury therapeutic can provide therapeutic effects.

E. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits comprising one or more of the disclosed peptides.

EXAMPLES

DiaCyt is a new platform technology to identify delivery agents that selectively transport a wide variety of therapeutic cargos into the CNS without physical disruption of the BBB. A selection platform has been developed that identifies peptide-based Molecular Transport Systems (MTS) that: enable passage into the CNS without breakdown of the barrier: carry therapeutics, including biological molecules such a antibodies, proteins, and nucleic acids, into the CNS without inactivating them during transport; and release the MTS-Cargo and distribute cargo throughout the CNS.

The concept is unique in two manners. First, the selection is an unbiased, phenotypic approach allowing us to select MTS with the key features described above. This will identify MTSs able to transverse the CNS barrier and release into the CNS. Furthermore, the selection requires transport of functional bacteriophage. Thus, identified MTSs carry biologic material through the cell without degradation of the cargo during the process.

The second unique feature is that the choroid plexus is targeted as opposed to the endothelial BBB. This is advantageous as it exploits the physiological structure and biological function of the choroid plexus (see Appendix) and overcomes barriers of delivery through the endothelial BBB which has been the focus in the field. Capillaries of the choroid plexus are fenestrated (leakier) and do not have astrocyte foot processes surrounding the blood vessels which allows passage of material out of the blood.

FIG. 1 shows that the BBB is a formidable biological obstacle. Access of drugs and biological therapeutics to CNS tissues through gaps between cells is not an option. The peptides, compositions and methods disclosed herein provide new paradigms for drug development. The choroid plexus produces cerebral spinal fluid (CSF). The epithelial cells have tight junctions which forms the blood cerebrospinal fluid barrier (BCSFB). Unlike the BBB, the capillaries are fenestrated (gaps between endothelial cells) which allow immune cells, proteins, and even pathogens to escape. The choroid plexus epithelial cells are specialized cells that transport ions, peptide hormones and proteins from the blood to the CSF. Tight junctions are absent in the ependyma, pia mater, and glia limitans, allowing paracellular diffusion between CSF and brain.

Figure 2:
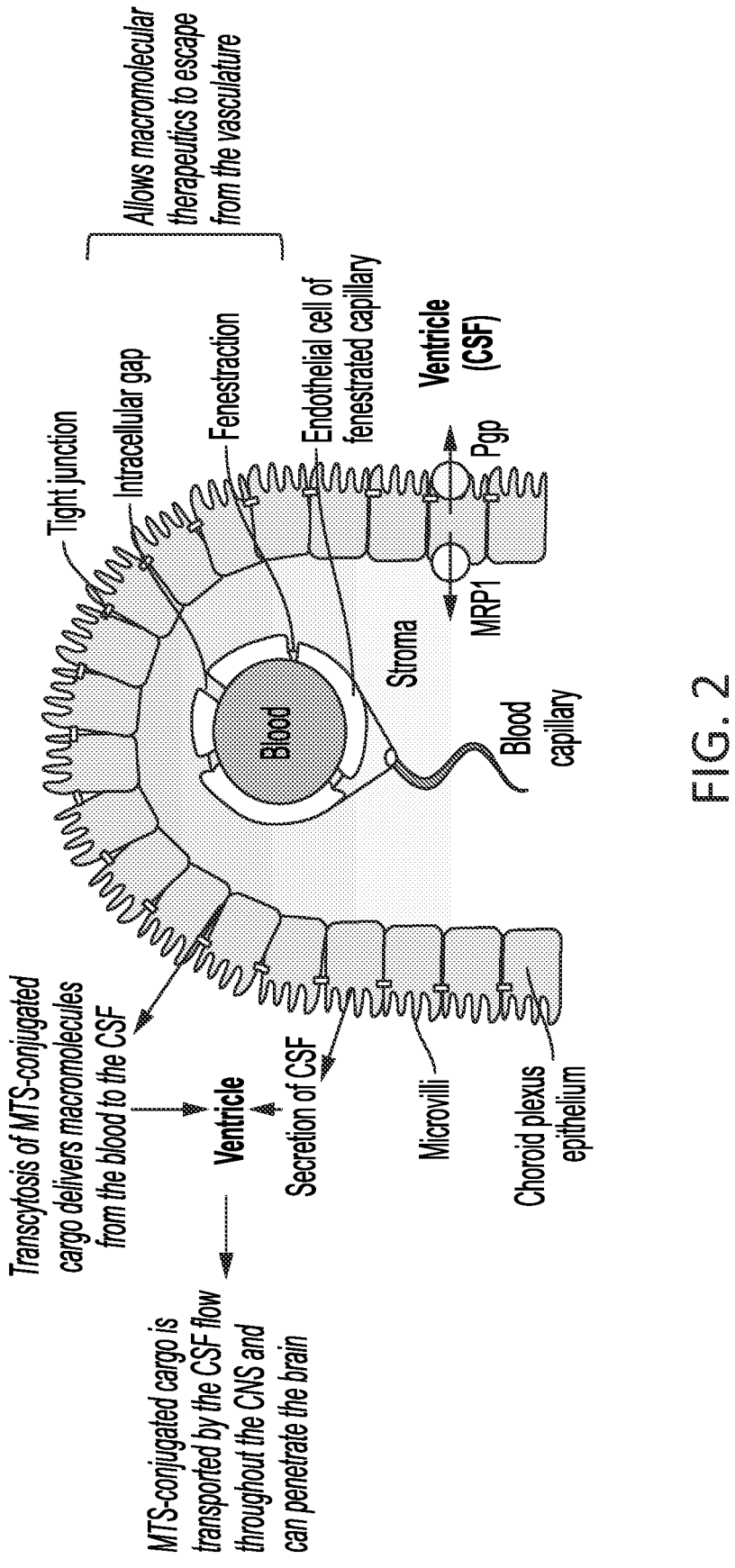
FIG. 2 is a schematic showing the important features of the choroid plexus as a point of transport into the CNS. The structural features of the fenestrated capillaries and the transcytosis activity of the choroid plexus epithelium underlie the functional differences between the choroid plexus and the BBB.

FIG. 2 shows a schematic of the capillaries in the choroid plexus and how they allow the transport of cargo into the CNS. Some of the structural advantages of targeting the choroid plexus is that the 1) capillaries are fenestrated (leakier) allowing passage of material out of the blood, and 2) there are no astrocyte foot processes surrounding the blood vessels. Some biological advantages of targeting the choroid plexus are that it exploits a natural role of the choroid plexus epithelial cells which is the transport of molecules, peptides, proteins, and cells into the CNS. Another biological advantage of targeting the choroid plexus is it transports cargo into the CSF which is then circulated throughout the CNS.

Figure 3:
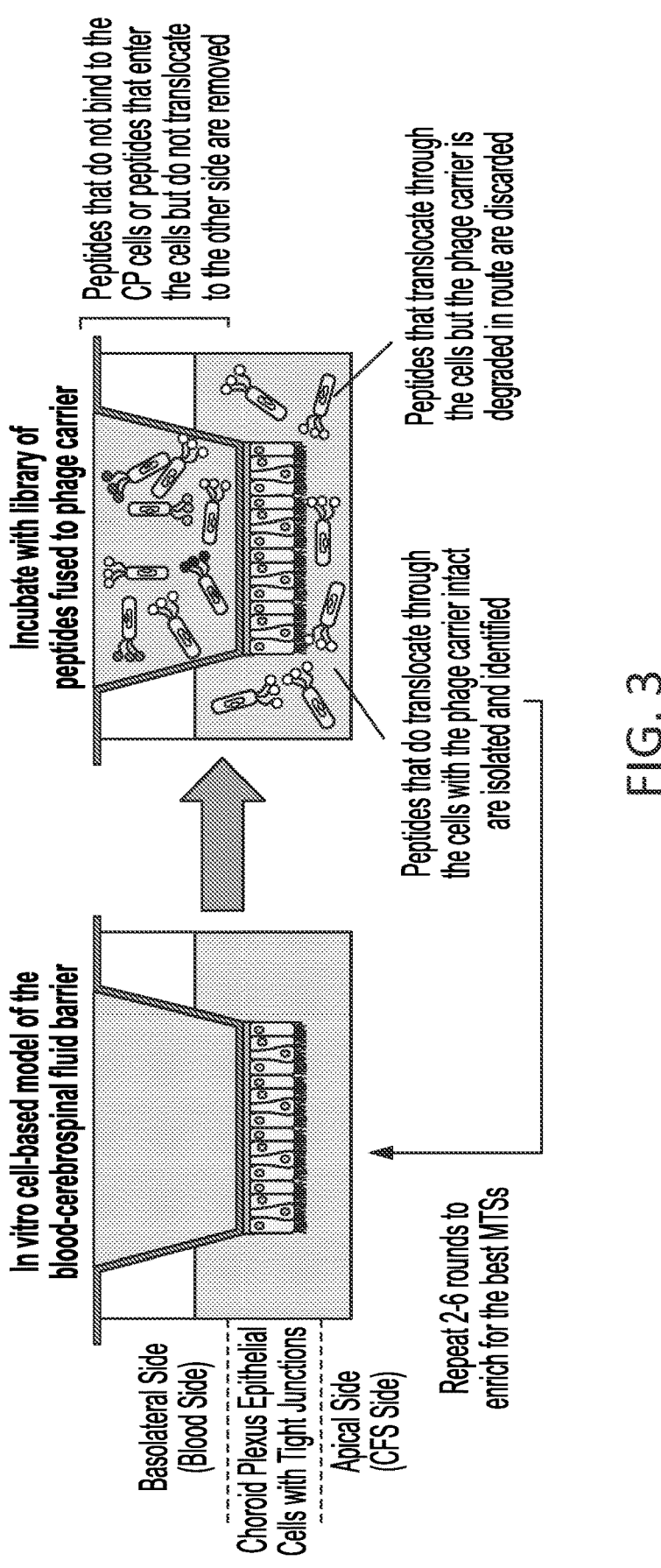
FIG. 3 shows experimental design for unbiased selection to identify MTSs that mediate functional transport activity.

One experimental design for unbiased selection to identify MTS peptides that mediate functional transport activity is shown in FIG. 3. The identified MTSs can be easily optimized by chemical means to generate MTSs fit to be used for cargo delivery to the CNS.

Figure 4:
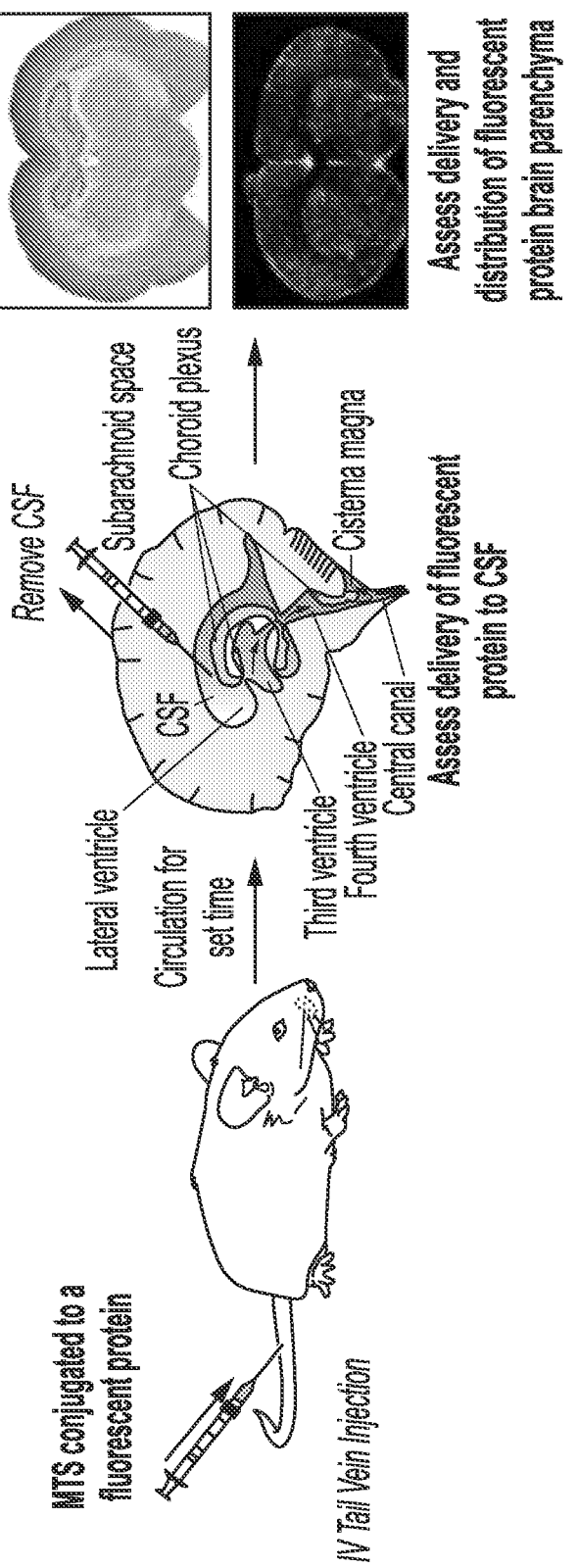
FIG. 4 shows an experimental design for confirmation of in vivo delivery of the MTS to the CNS.

One experimental design for confirmation of in vivo delivery of the MTS to the CNS is shown in FIG. 4. This design allows for selection of MTSs that mediate functional transport across the cellular barrier via a pathway that protects the cargo from degradation.

Figure 5:
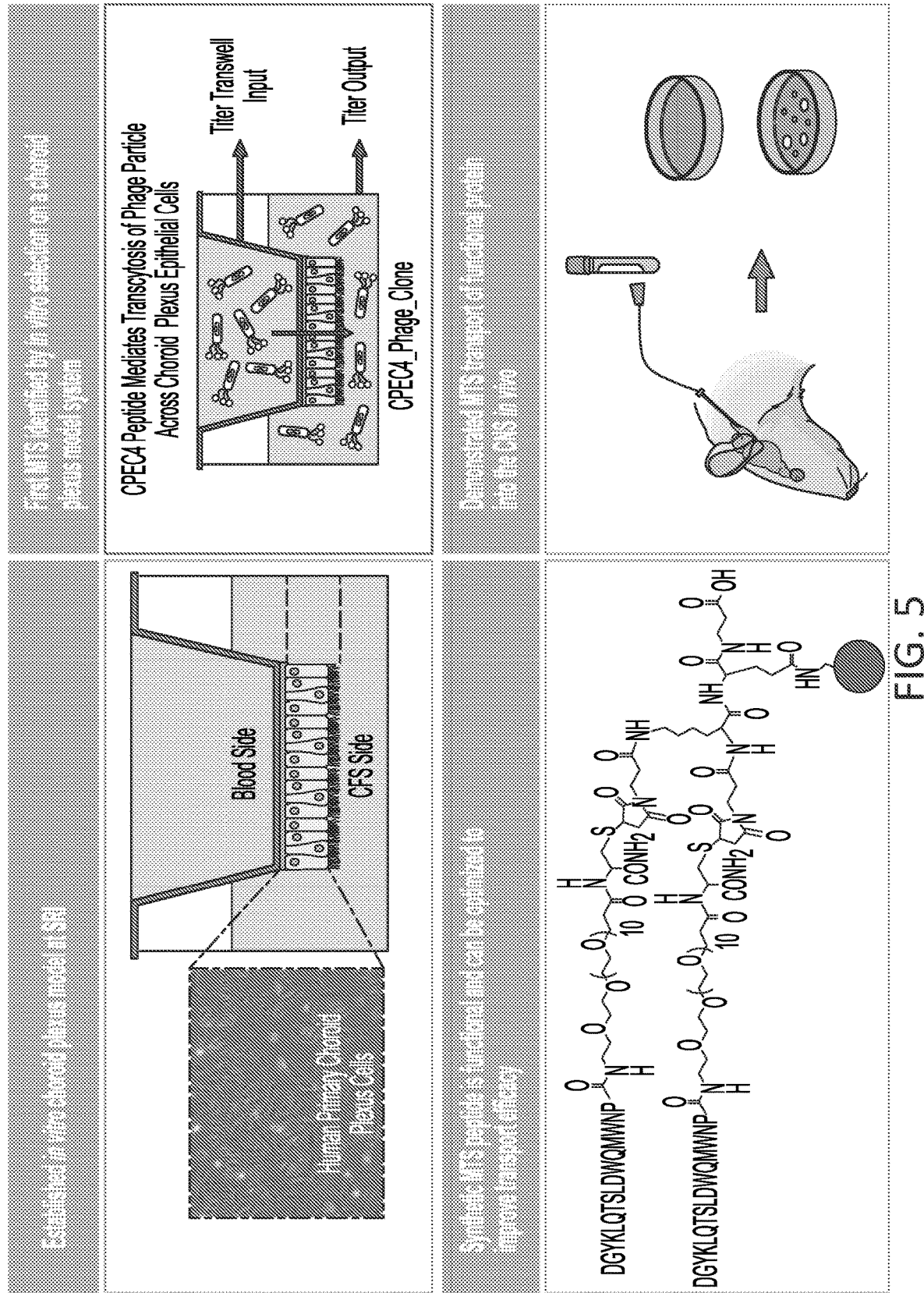
FIG. 5 illustrates how an MTS system was developed.

FIG. 5 outlines how a system was developed to identify MTS peptides. This system identified one MTS Phage clone with the ability to transcytose in an in vitro model and enter the CSF in an in vivo model. Data with the synthetic MTS_CPEC4 (DGYKLQTSLDWQMWNP (SEQ ID NO:2)) showed activity in vitro and in vivo.

Figure 6:
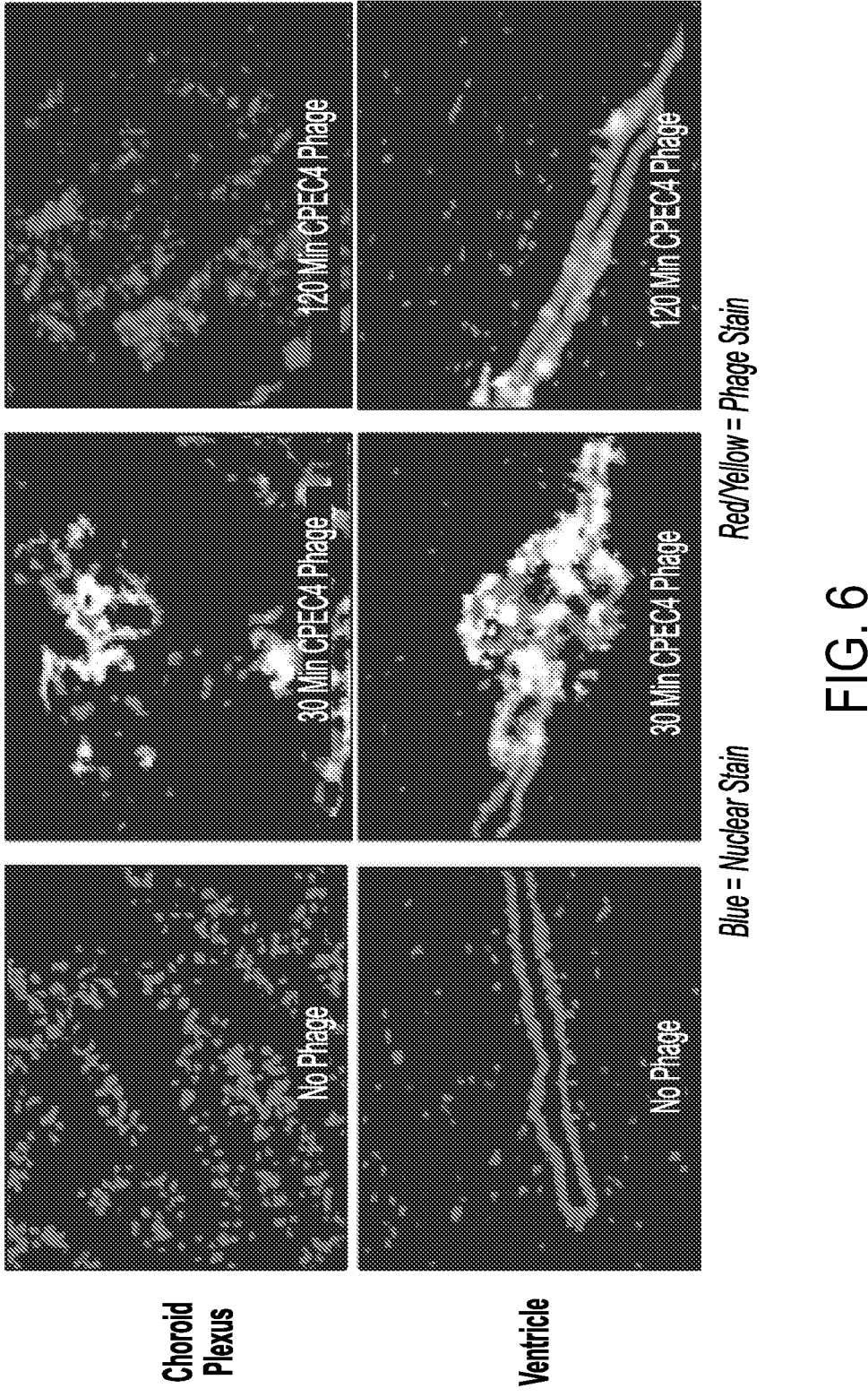
FIG. 6 show tissue staining of CPEC4 Phage clone in the choroid plexus and ventricle. CPEC4 Phage clone is the phage clone that expresses the CPEC4 peptide (SEQ ID NO: 2).
Figure 7:
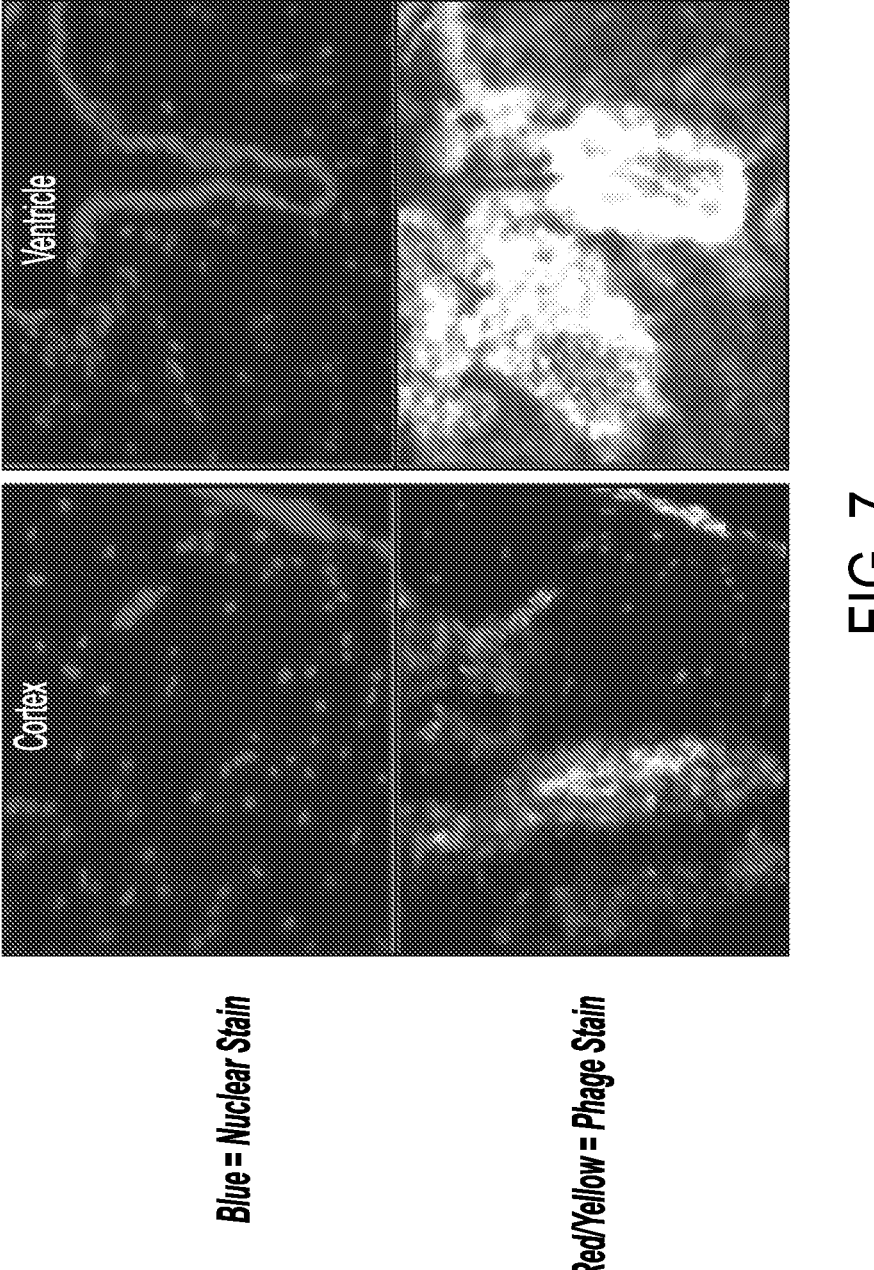
FIG. 7 shows tissue staining of CPEC4 Phage clone outside of the ventricular system in the brain.
Figure 8:
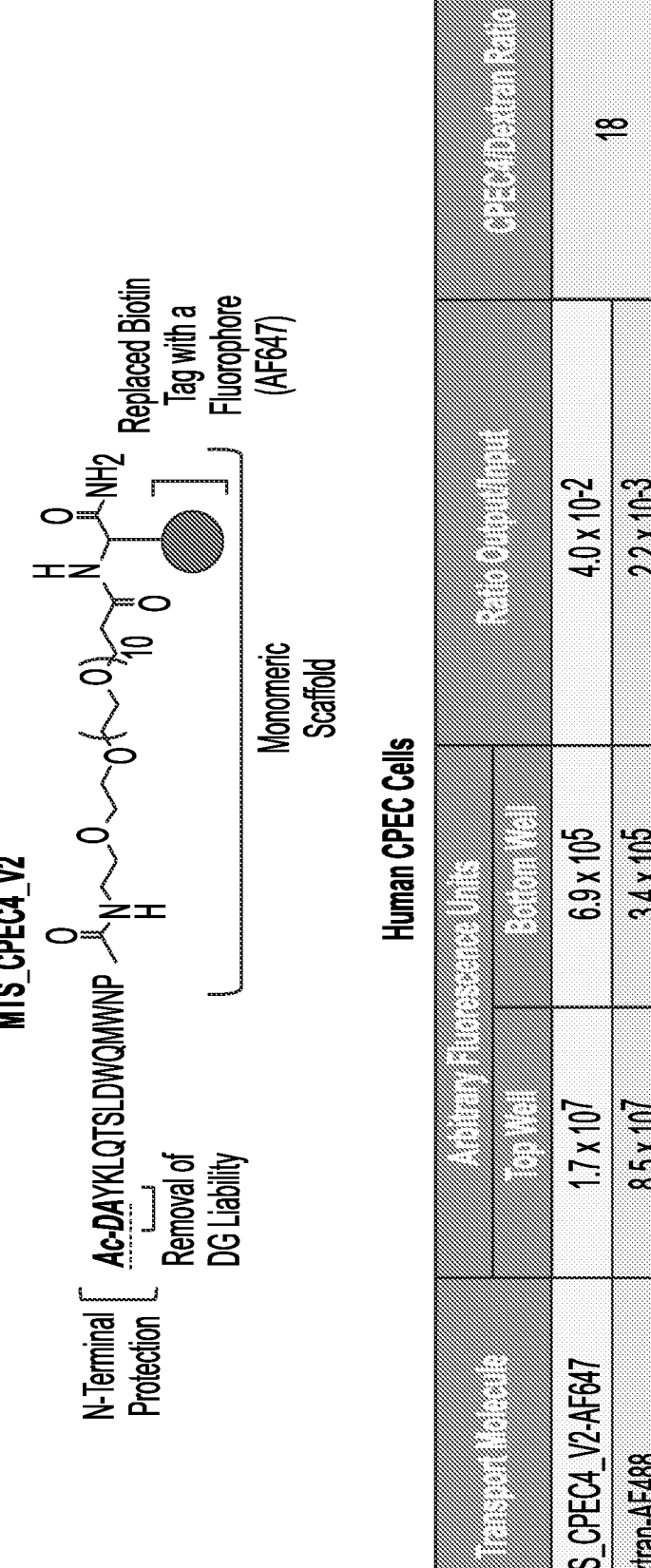
FIG. 8 shows peptide engineering improves solubility and stability while maintaining transport capabilities.
Figure 9:
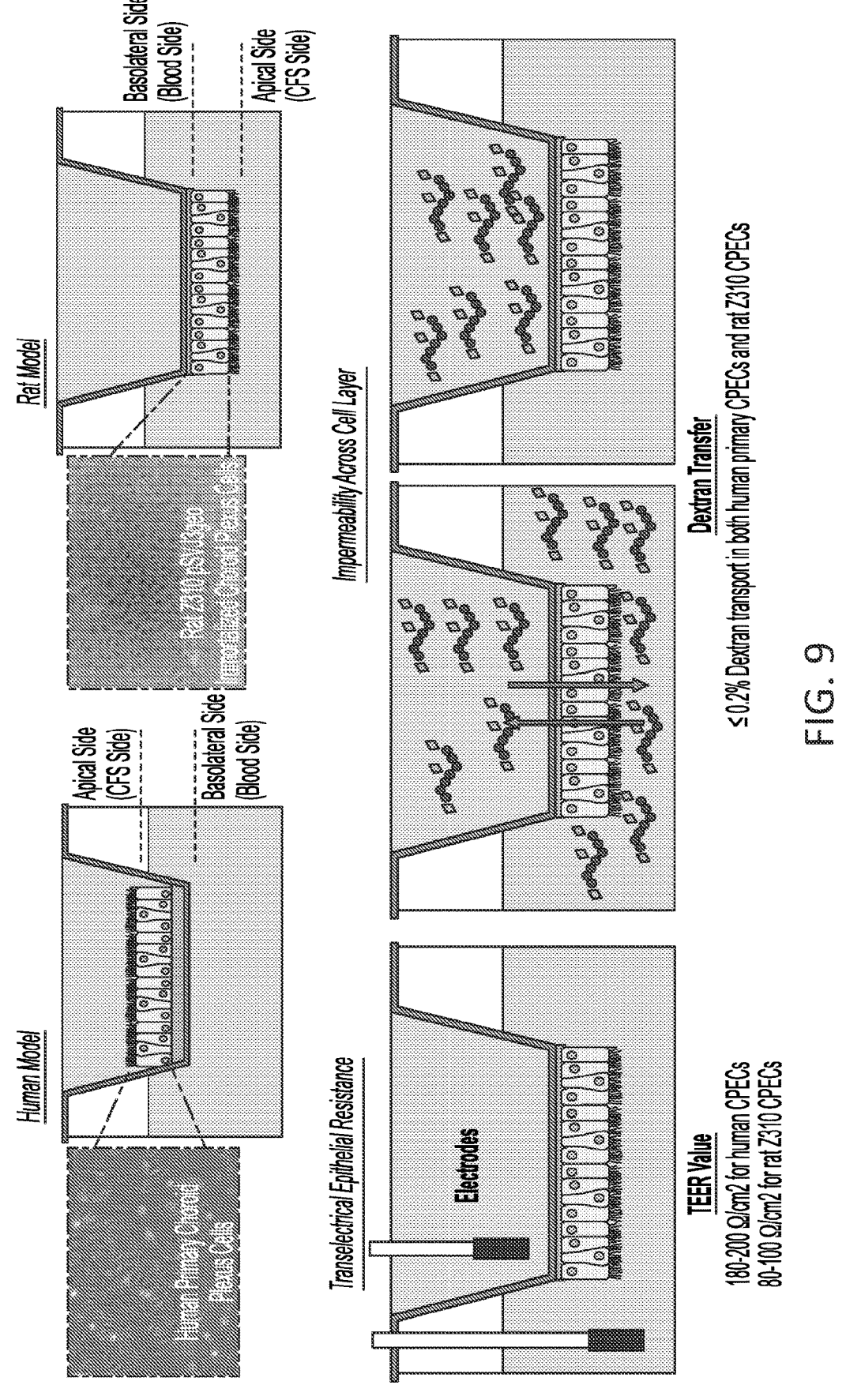
FIG. 9 shows a transwell model using primary human choroid plexus epithelial cells maintains features of the CNS barrier.

FIG. 6 show tissue staining of CPEC4 Phage clone in the choroid plexus and ventricle and FIG. 7 shows tissue staining of CPEC4 Phage clone outside of the ventricular system in the brain. This shows that delivery of an MTS-cargo to the CNS will result in transport of cargo to other regions of the brain. The phage clone was injected i.v. via the tail vein in a rat. After allowing the phage clone to circulate for a set period of time, the animal was terminally perfused and the brain isolated. After fixation, the brain was sliced and processed for immunohistochemistry. Phage was detected using an anti-M13 phage primary antibody. The blue stain is a nuclear stain. Phage staining is observed in the ventricles and surrounding tissues indicating transport of the phage clone into the CSF.

This data established an in vitro model of the choroid plexus using human primary chorid plexus epithelial cells that replicated the tight junctions found in the human choroid plexus. A rat model was developed as well. Selection to identify a phage clone from the library that crosses the choroid plexus epithelial barrier has also been informed. The peptide was synthesized outside of the context of the phage and it was demonstrated that the peptide retains its transport activity and can carry small molecules and proteins across the barrier. The phage clone was transported into the CSF selectively and data supported similar transport for the MTS peptide.

Once MTS peptides have been identified, they can be optimized by several means, including chemical modification. Optimization can increase solubility, stability, brain distribution, biodistribution, cellular transport, or circulation time. Desired outcomes of using the MTS are at least 2.5% of the injected dose present in the CNS although greater than 5% of the injected dose present in the CNS The current studies screen and validate in an in vitro transwell, provide targeting in an animal model using multiple approaches to fully validate efficiency of delivery (real time CSF analysis, ex vivo analysis of CSF with accompanying histology, radiolabeling, and/or imaging), and assess the effects of different cargo on MTS delivery efficiency (peptide, protein, and nucleic acid).

Figure 10:
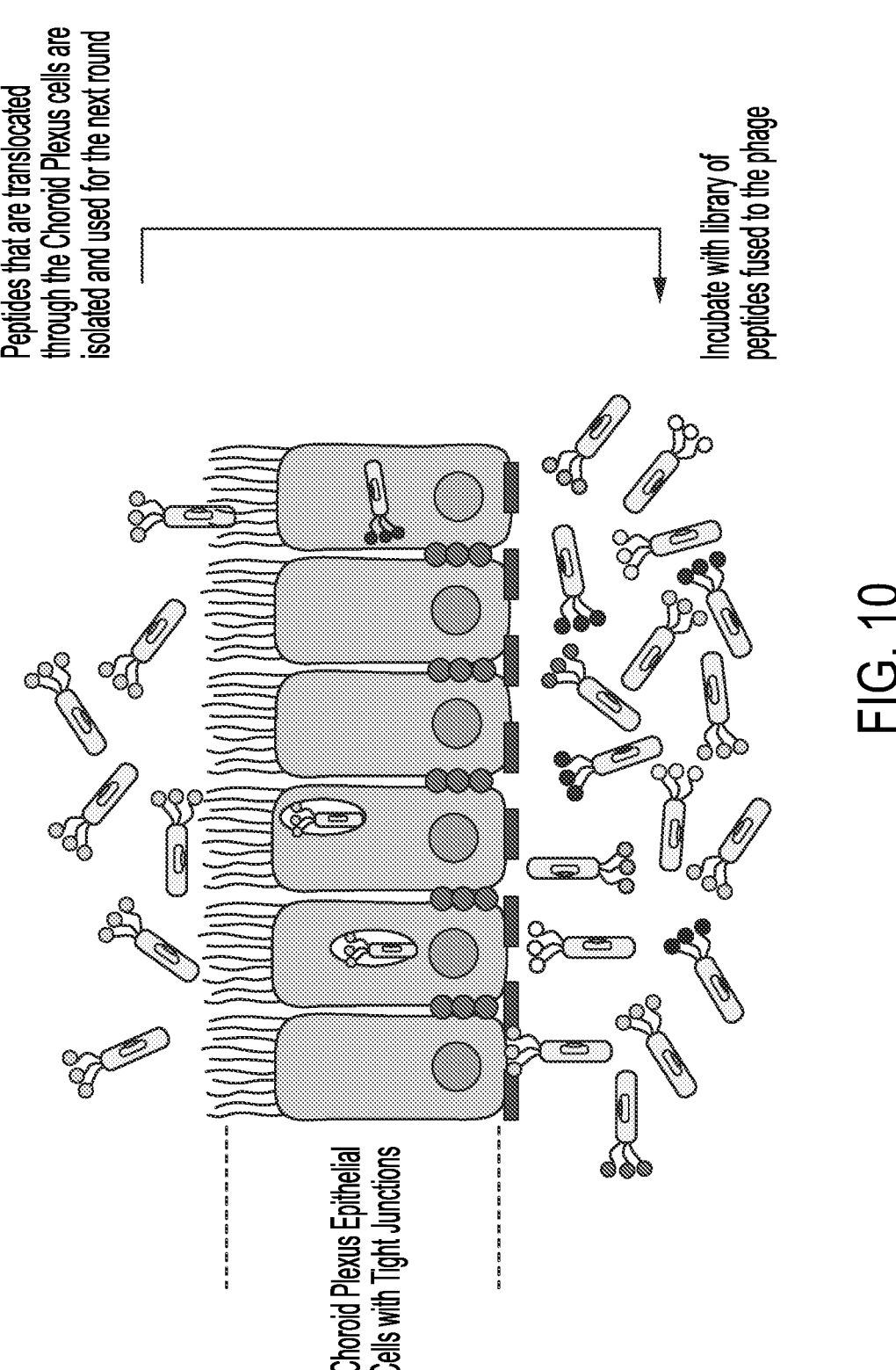
FIG. 10 show an unbiased selection to identify MTSs that mediate functional transport activity.

FIG. 10 is a schematic of the experimental design using a monolayer of rat choroid epithelium (Z310 cells), inside the transwell bucket, for unbiased selection to identify MTS peptides that mediate functional transport activity. The Z310 cells were exposed to a phage library on their basal side (mimicking the blood side of the choroid plexus) with transported phage present on the apical (CSF side, inside bucket) after incubation. Phage were also recovered from cell lysates after this incubation. The library used in this selection expressed 16-mer peptides generated by random addition of synthetic codons.

Figure 11:
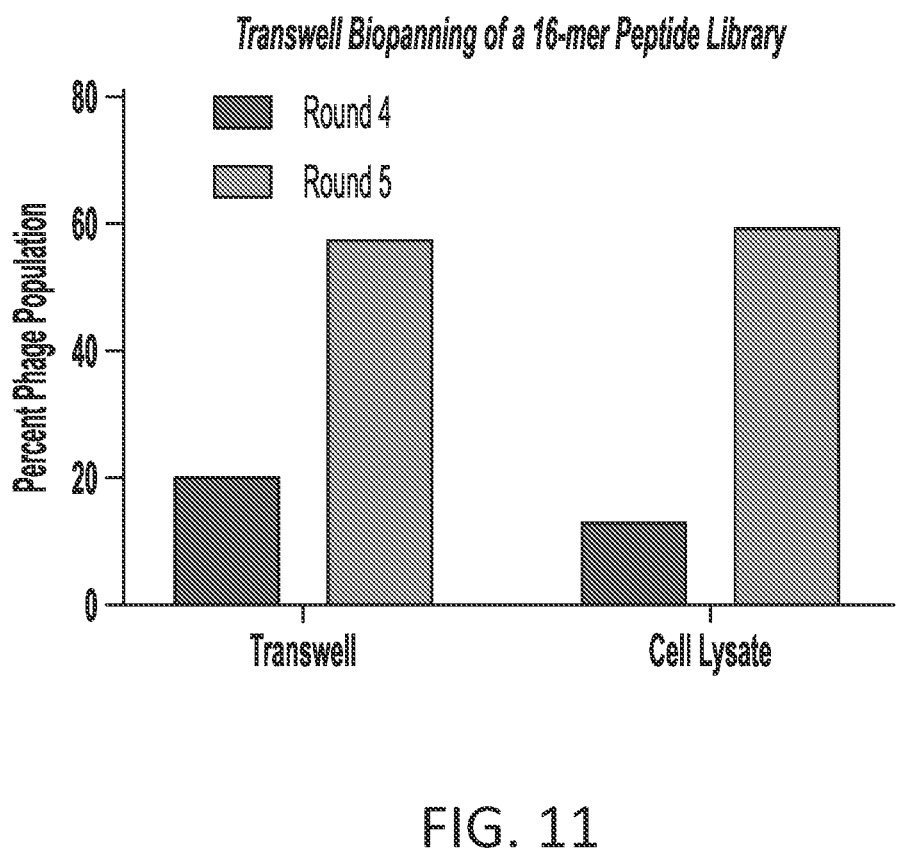

FIG. 11 summarizes the abundance of the phage clone encoding the MTS_CPEC4_V1 peptide sequence (SEQ ID NO:2) among the sequences obtained from 96 individual phage clones submitted for DNA sequencing from transwell and lysate samples in panning round 4 and 5. MTS_CPEC4_V1 was selected from a random 16-mer peptide library with an initial complexity of $2.6 \times 10^{10}$. This peptide clone was the predominate sequence observed in panning rounds 4 and 5 of its selection. The frequency of observing this specific sequence in the output from rounds 4 and 5 is summarized in FIG. 11. As shown, this sequence was observed in both the transwell transported output as well as the lysate of cells at the end of the timed incubation. The total number of CPEC4_V1 clones observed the output of panning rounds 4 and 5 was 144 of 365 sequences. The only other peptide observed in both transwell output and cell lysate from both rounds but at a much lower frequency (6/365).

Figure 12:
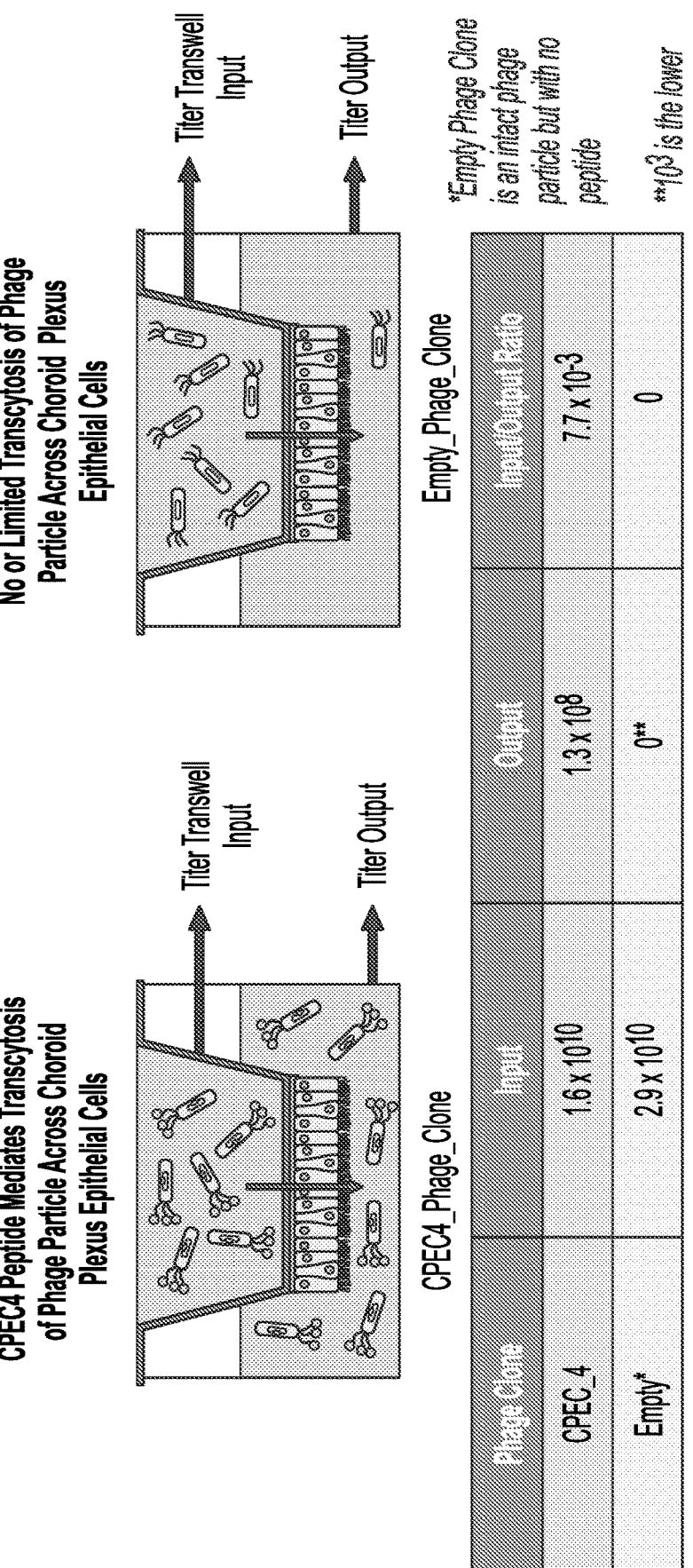
FIG. 12 shows the validation of CPEC4 phage clone transport through human choroid plexus cells in an in vitro system.

Transwell selections on human primary choroid plexus epithelial cells have been completed and resulted in lead peptides (FIG. 12). CPEC4_Phage clone sequence DGYKLQTSLDWQMWNP (SEQ ID NO:2) was the lead peptide sequence in these studies. CPEC4 phage clone is enriched as multiple rounds of panning were performed. CPEC4 phage clone is selected from the transwell indicating transport and release. CPEC4 phage clone can be seen in the cell lysate indicating active transport through the cells and not "around" the cells.

FIG. 12 shows that the CPEC4 peptide (SEQ ID NO:2) mediates transport of a large phage particle across choroid plexus epithelial cell layer. The phage clone remains viable during the cellular transport.

FIG. 13 represents a dimer of the CPEC4 peptide. The CPEC4 peptide was synthesized as a dimer and having a biotin handle that allows for attachment of fluorescently labeled proteins.

Figure 14:
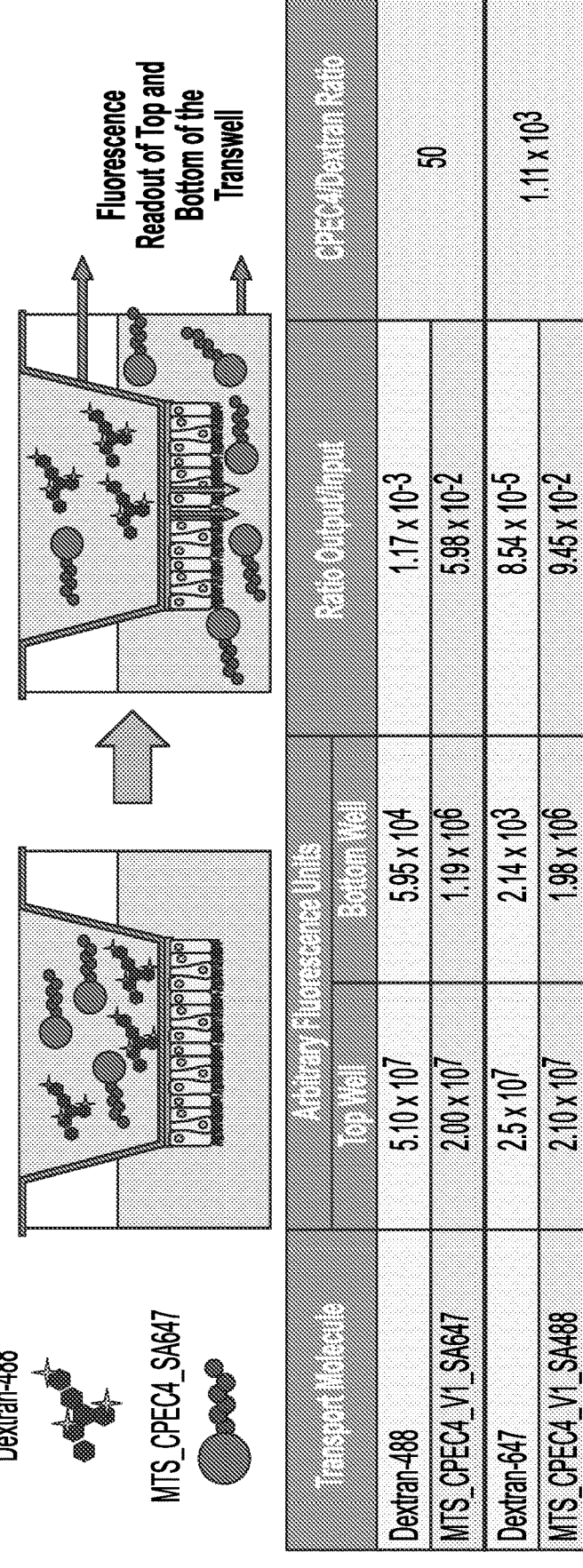
FIG. 14 shows the validation of a CPEC4 phage clone transport through human choroid plexus cells in an in vitro system.

FIG. 14 shows that MTS_CPEC4_V1 (SEQ ID NO:2) mediates transport of a fluorescent molecule across human choroid plexus in vitro model. 6-9% of the protein is transported across the cell layer. Tight junctions remain intact as witnessed by lack of dextran transport and maintenance of transepithelial resistance at the end of the experiment.

FIG. 15 is an in vitro transwell assay used to determine the ability of the MTS_CPEC4 phage clone or peptide to cross a choroid plexus barrier model derived from a Rat (Z310 cells). The amount of input placed on one side of the barrier (the "blood" side) and the amount that passes through the cells to the other side (the CSF side) is measured. The top table represents the data for the phage clone. The empty phage has no MTS peptide attached. The amount of phage in each side of the transwell is determined by bacterial titering. The bottom table represents the data for the synthetic peptide. Here the peptide is labeled with a fluorophore so the peptide on either side of the barrier can be measured. Dextran-dye (such as Alexa Fluor 488) is used as a control molecule. This molecule should not pass through the transwell and assures that the choroid plexus model is valid.

Figure 16:
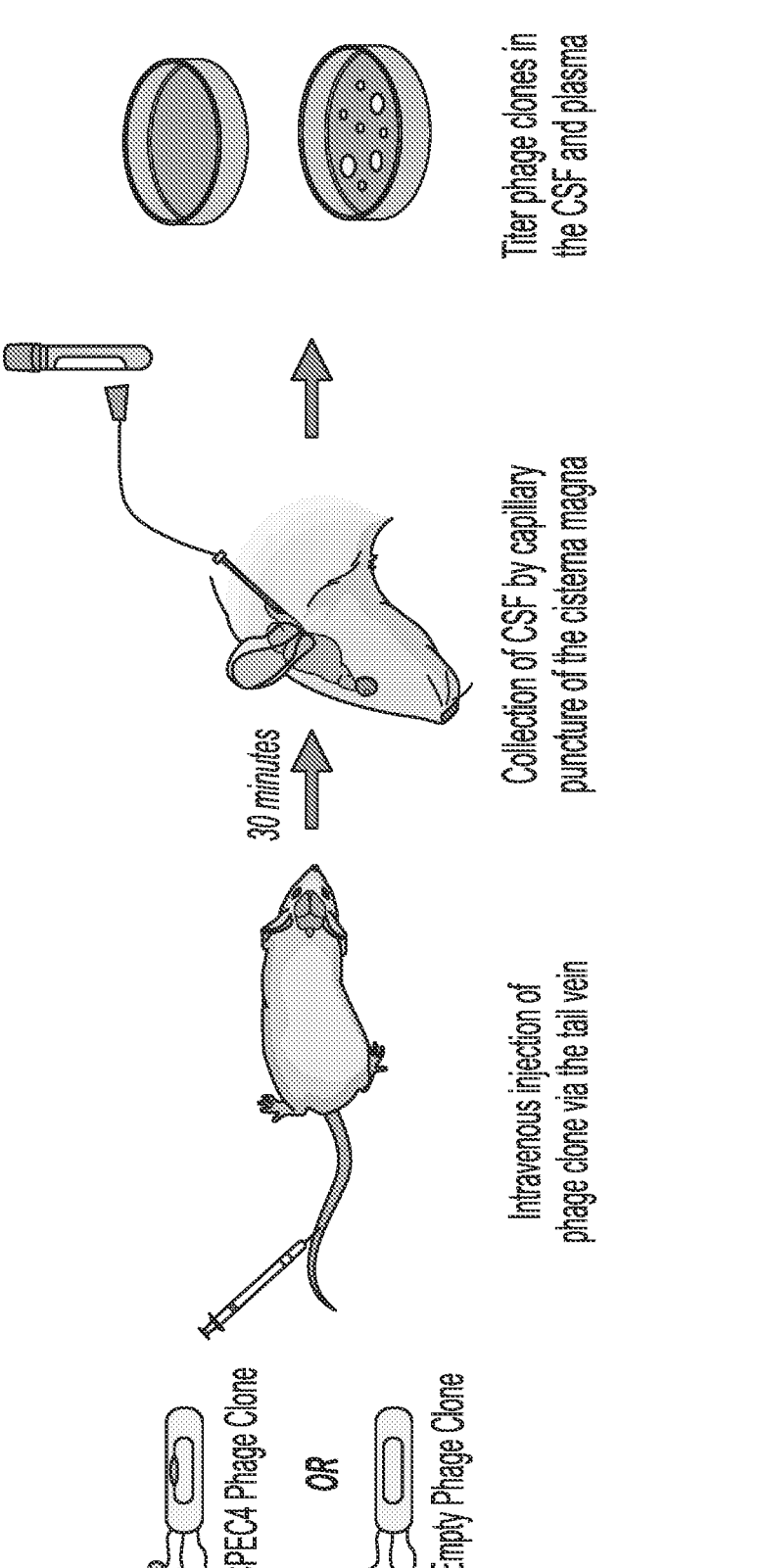
FIG. 16 shows confirmation of in vivo delivery system in the CNS.

FIG. 16 diagrams how the MTS delivery system targets the CNS. After tail vein injection of mice, CSF can be removed from the brain by capillary puncture of the cisterna magna and the presence of phage can be determined.

Figure 17:
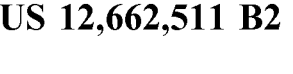
FIG. 17 shows that CPEC4 phage clone preferentially accumulates in the CSF of rats compared to a non-targeted empty phage clone.

FIG. 17 shows the CPEC4 phage clone preferentially accumulates in the CSF compared to a control phage and therefore can mediate transport to the CSF. The phage clone remains viable during the transport to the CSF.

Figure 18:
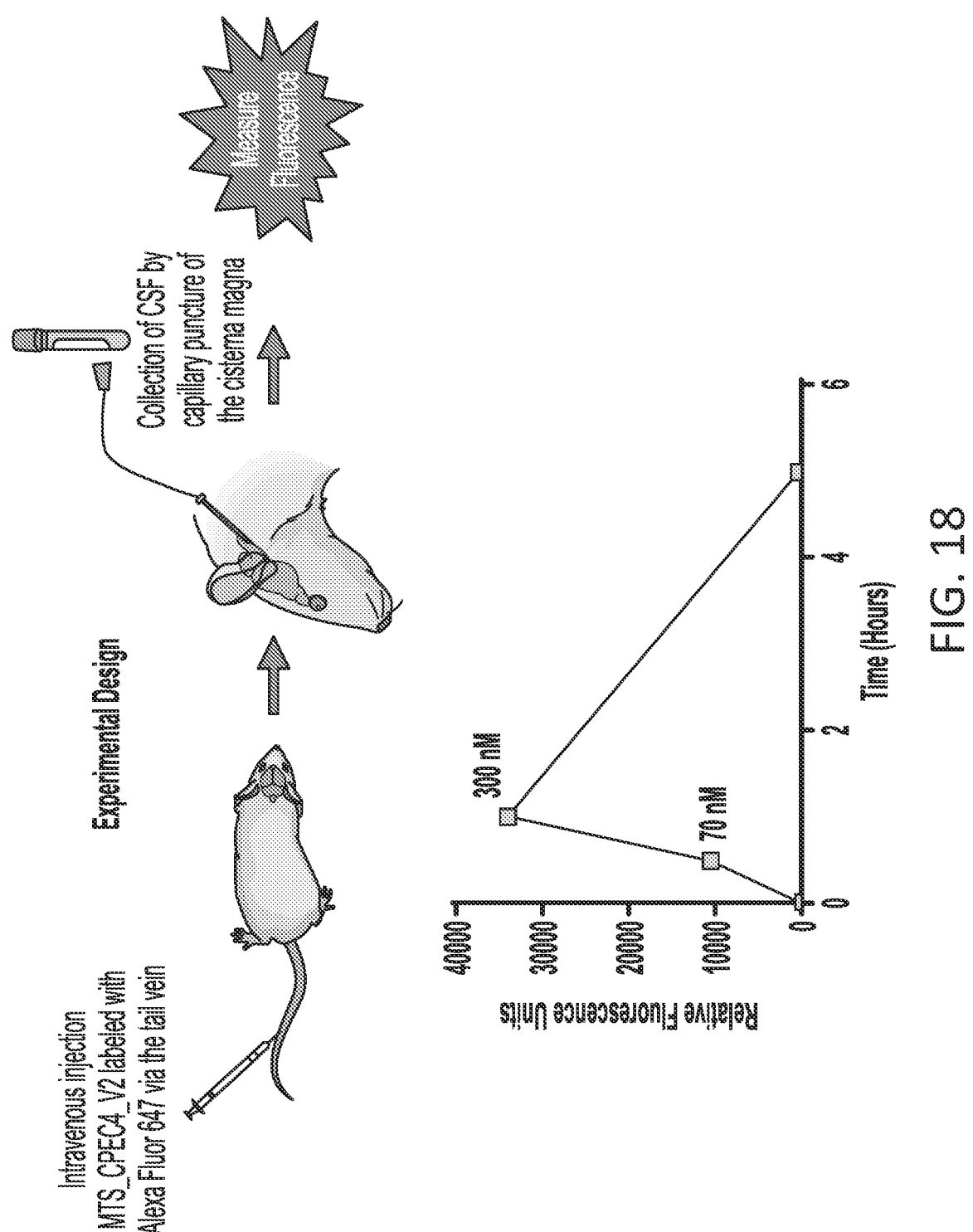
FIG. 18 shows that MTS-CPEC4_V2 accumulates in the CSF of rats. MTS-_CPEC4_V2 comprises an MTS peptide having the sequence of DAYKLQTSLDWQMWNP (SEQ ID NO: 1).

FIG. 18 shows the experimental design and end result MTS-CPEC4_V2 (SEQ ID NO: 1) accumulating in the CSF of rats after tail vein injection.

Figure 20:
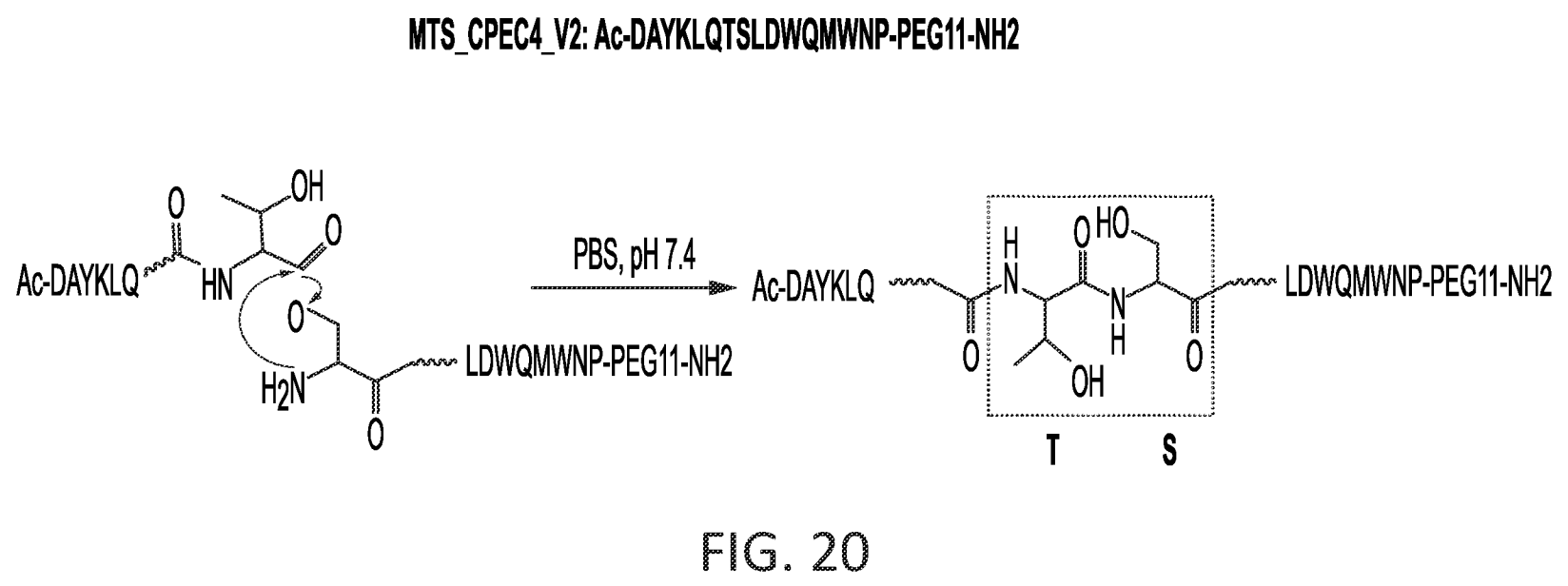

Although the MTSs were able to be synthesized, it was difficult to synthesize more than a milligram of quality monomeric peptide and the dimeric peptide was even more challenging. It was determined that inserting the "TS" in the middle of the MTS_CPEC4_V2 sequence using an isoacyl Thr-Ser dipeptide provided beneficial results (FIG. 20).

Figure 21:
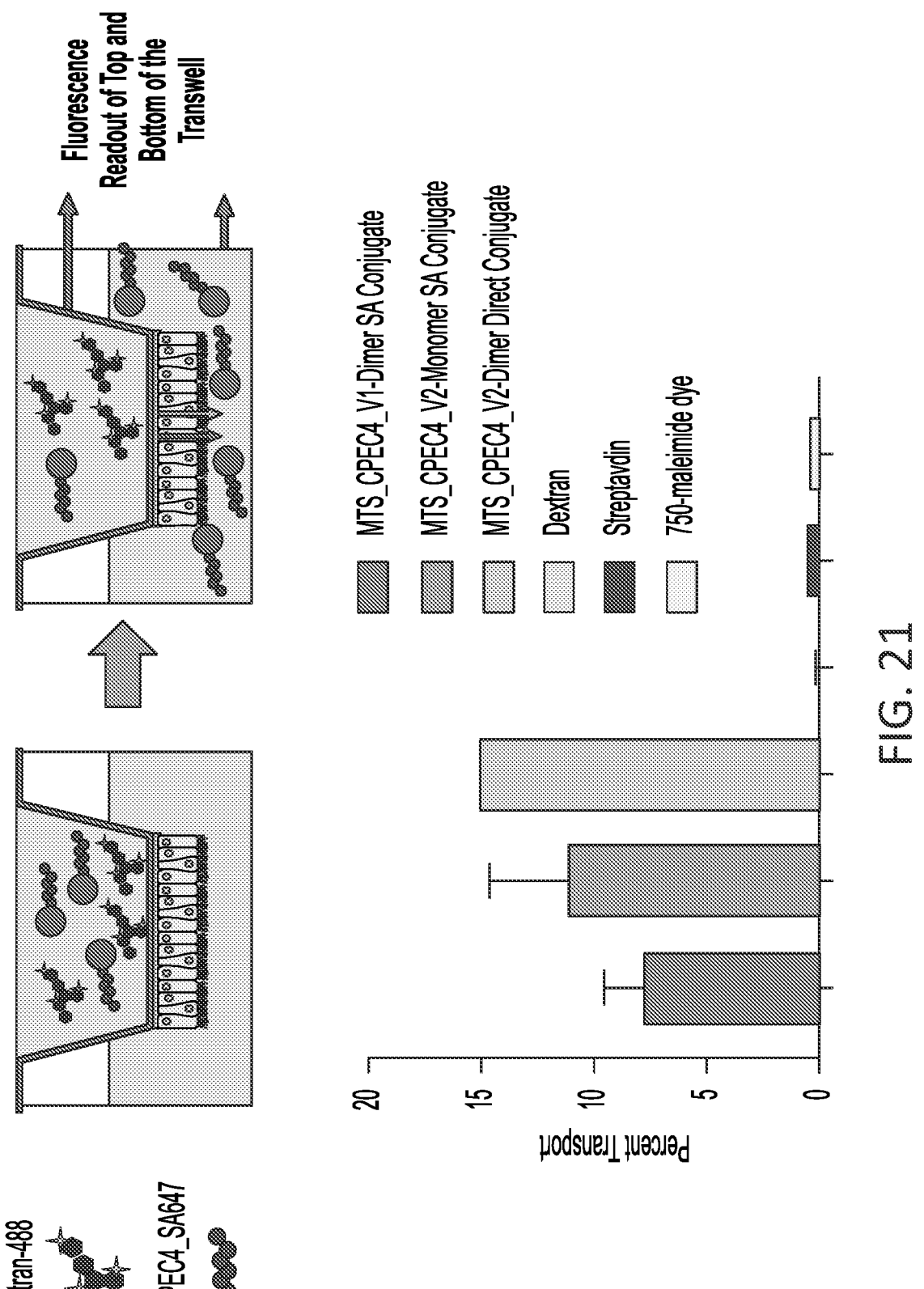
FIG. 21 shows the percent transport using MTS_CPEC4_V2 dimer. MTS-CPEC4_V1 dimer comprises two MTS peptides each having the sequence of DGYKLQTSLDWQMWNP (SEQ ID NO:2): MTS_CPEC4_V2 monomer comprises the MTS having the sequence of DAYKLQTSLDWQMWNP (SEQ ID NO:1); MTS_CPEC4_V2 dimer comprises two MTS peptides each having the sequence of DAYKLQTSLDWQMWNP (SEQ ID NO: 1).

As shown in FIG. 21, CPEC4_V1 (SEQ ID NO:2) and CPEC_V2 (SEQ ID NO:1) are efficiently transported across a monolayer of choroid plexus cells with either chemical (AF647 dye) and protein (50 kDa Streptavidin) cargoes. The integrity of the monolayer with tight junctions is observed by the lack of diffusion or transport of low a molecular weight dye (750) maleimide), a 10 kDa dextran polymer, or larger protein (50 kDa). In the SA conjugate, the MTS has a biotin in the core structure. The biotin is then conjugated to a streptavidin protein labeled with a fluorophore. The direct conjugate means the fluorophore has been covalently linked to the MTS on the core (i.e. does not use the biotin/streptavidin linking).

Figure 22:
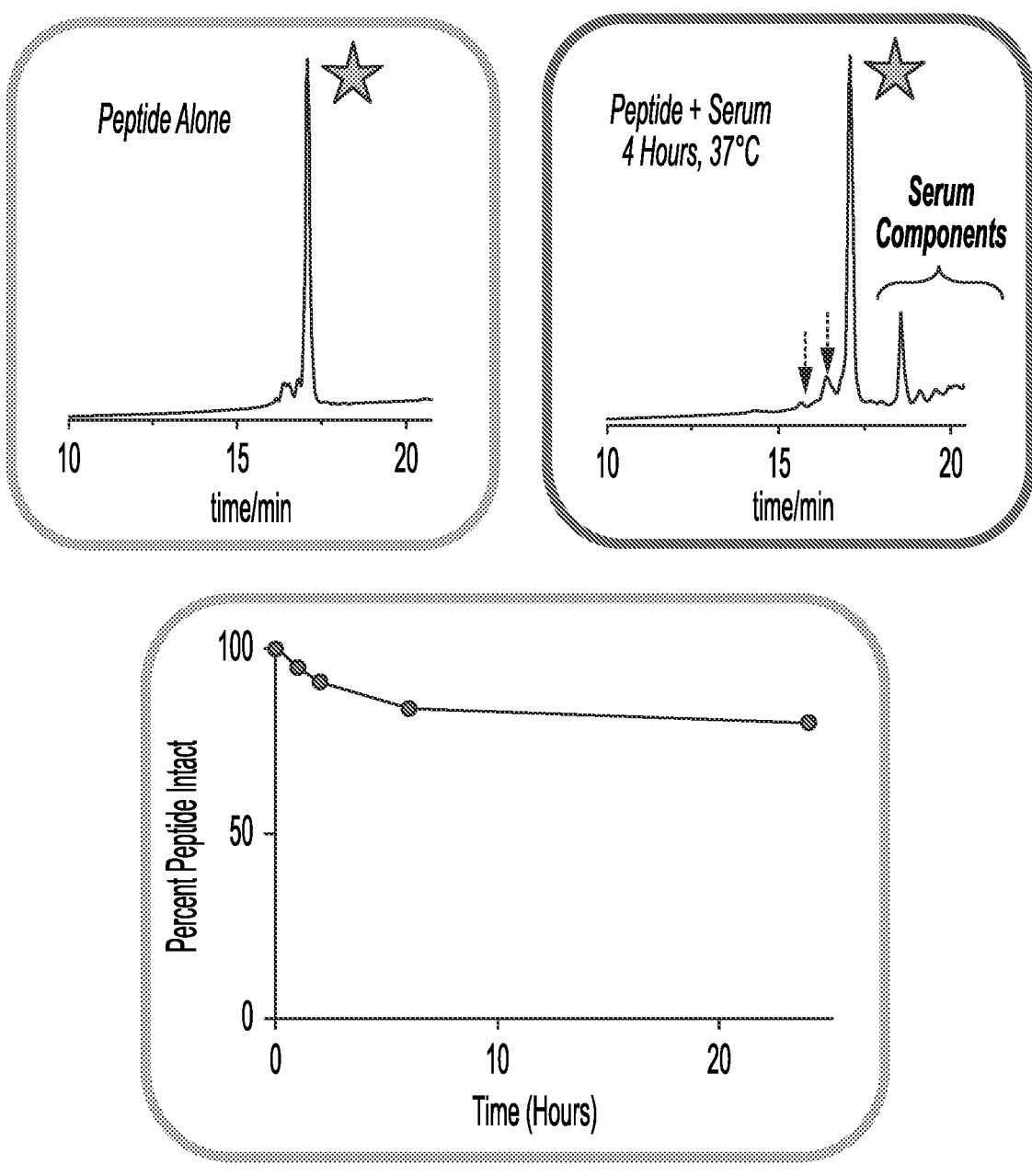
FIG. 22 shows that MTS_CPEC4_V2 is stable in serum. MTS_CPEC4_V2 comprises an MTS peptide having the sequence of DAYKLQTSLDWQMWNP (SEQ ID NO:1).

The stability of the different MTS sequences is important. FIG. 22 shows that MTS-CPEC4_V2 is stable in serum. 80% of the peptide remains intact at 24 hours. Modifications were mapped by MS. The MS data indicate the NP-PEGH11 is lost with possible oxidation of Methionine or Tryptophan.

Figure 23:
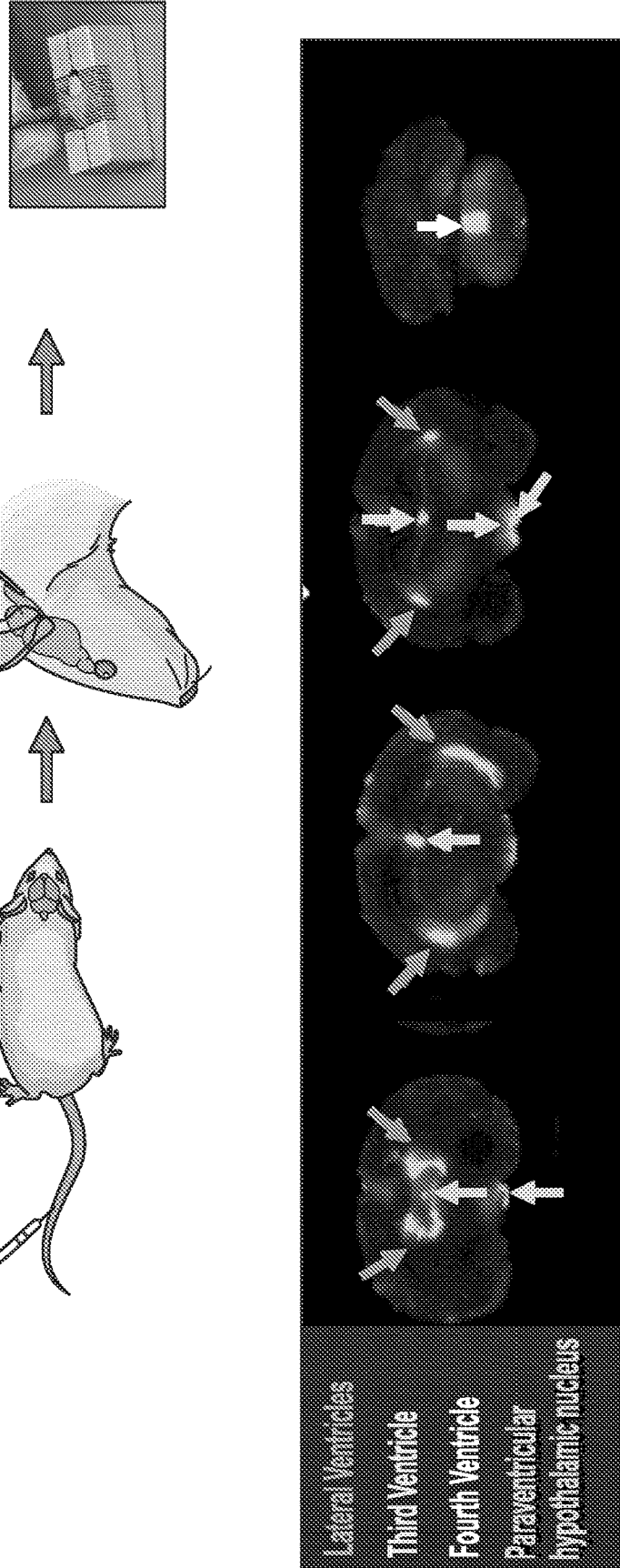
FIG. 23 shows in vivo use of MTS_CPEC4_V2. MTS_CPEC4_V2 comprises an MTS peptide having the sequence of DAYKLQTSLDWQMWNP (SEQ ID NO:1).

MTS_CPEC4_V2 (SEQ ID NO: 1) dimers have been used in in vivo experiments as shown in FIG. 23. The MTS is distributed throughout the ventricular system of the brain indicating that the MTS has crossed from the blood stream into the CSF. The MTS is labeled with a dye that allows us to visualize its location. It is injected IV into the tail vein of a rat. After the indicated time, the CSF is isolated from the cisterna *magna*. The brain is harvested. After a fixation period, the brain is sliced in 1 mm coronal segments (front to back). The individual slices of the brain are imaged using fluorescence to locate the regions of peptide accumulation.

Figure 24:
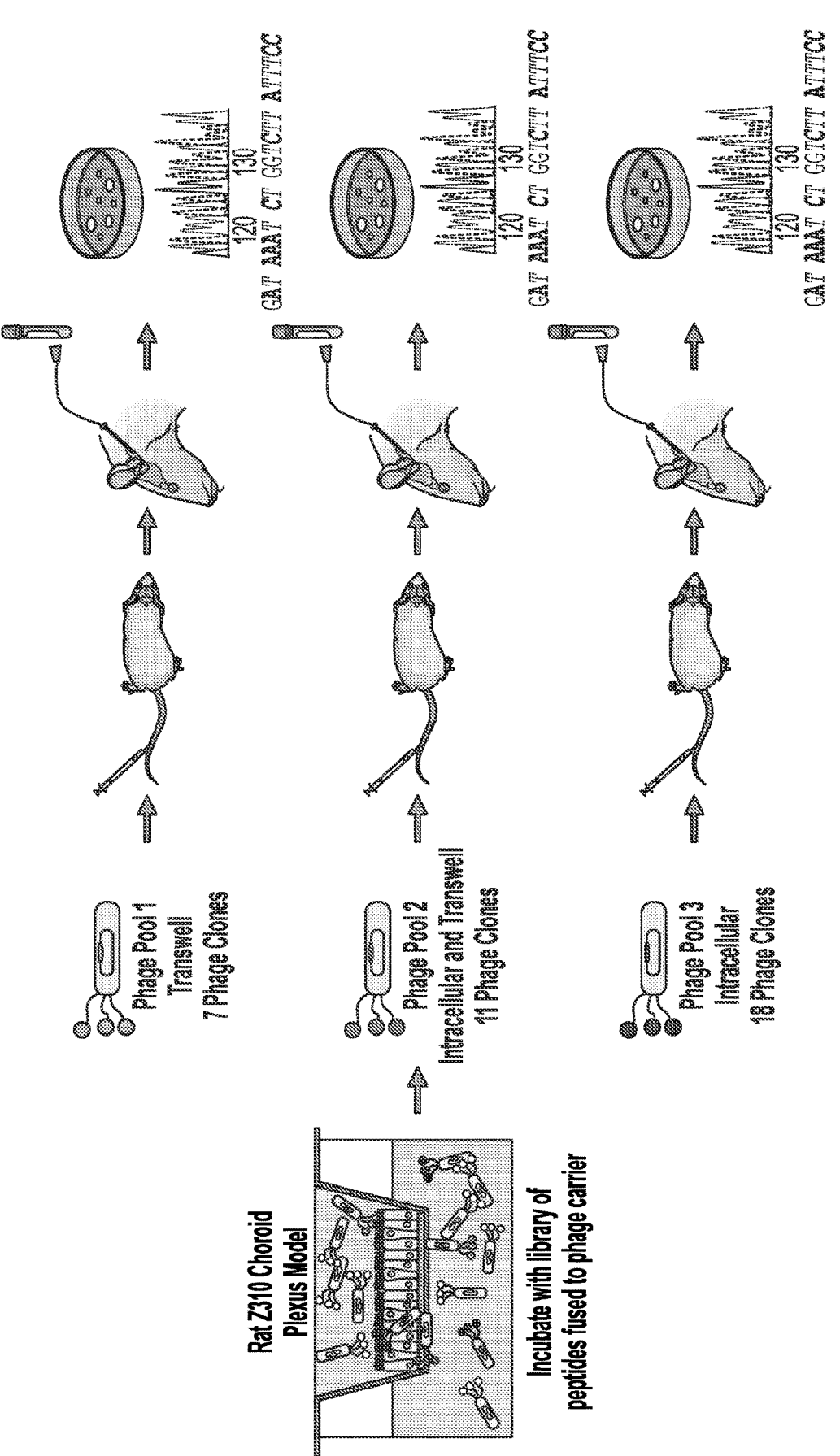
FIG. 24 is the experimental design of in vitro and in vivo selection of lead MTS peptides.
Figure 25:
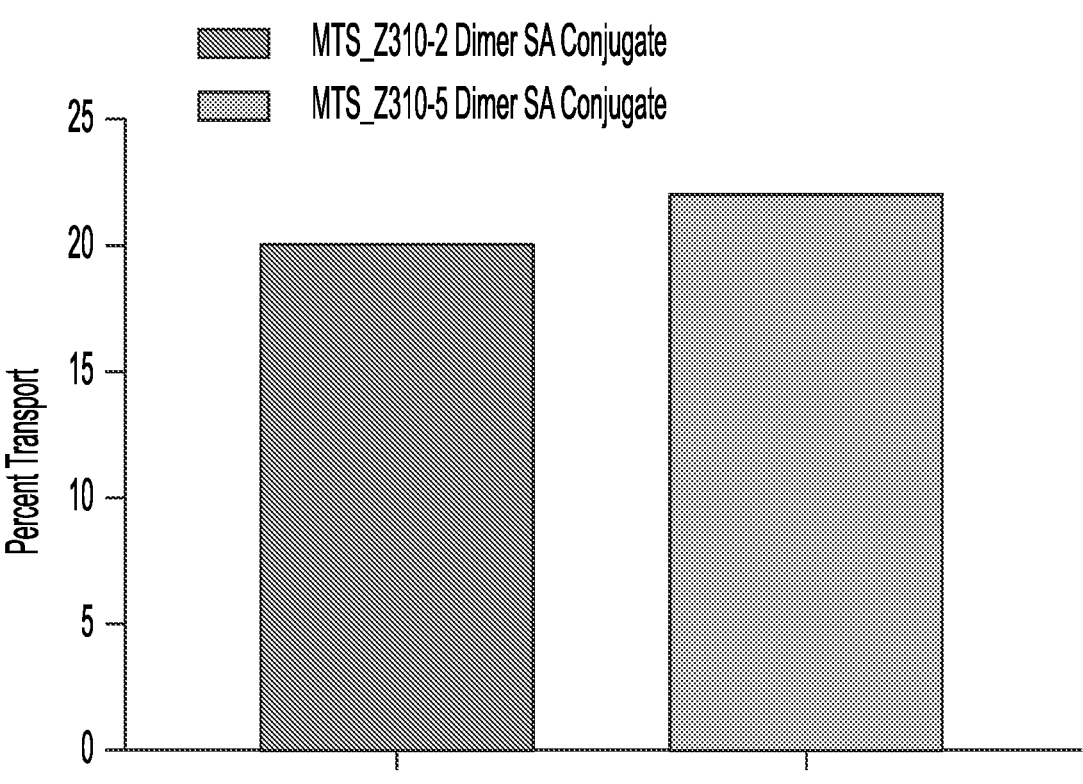
FIG. 25 shows MTS_Z310-2 and MTS_Z310-5 peptides transport protein cargo across rat choroid plexus epithelial cells. MTS_Z310-2 comprises an MTS peptide having the sequence of FPSWTSKNQQWTNQRQ (SEQ ID NO:4): MTS_Z310-5 comprises an MTS peptide having the sequence of SKETYSMNAQRQHERS (SEQ ID NO:7).

Other lead MTS peptides were examined using a transwell transport set up with rat choroid plexus cells (FIG. 24). Eight phage clones were enriched in the CSF. Individual phage clones were then tested for transcytosis in vitro on Z310 choroid plexus cells and CSF accumulation in rats. MTS_Z310-2 (SEQ ID NO:4) and MTS_Z310-5 (SEQ ID NO:7) phage clones were carried forward for further evaluation. FIG. 25 shows that MTS_Z310-2 and MTS_Z310-5 peptides transport protein cargo across rat choroid plexus epithelial cells. The 20% transport is better than that seen with CPEC4. Based on alanine scanning, the underlined portion of MTS_Z310-5 has been identified as the key peptide region responsible for activity.

Figure 26:
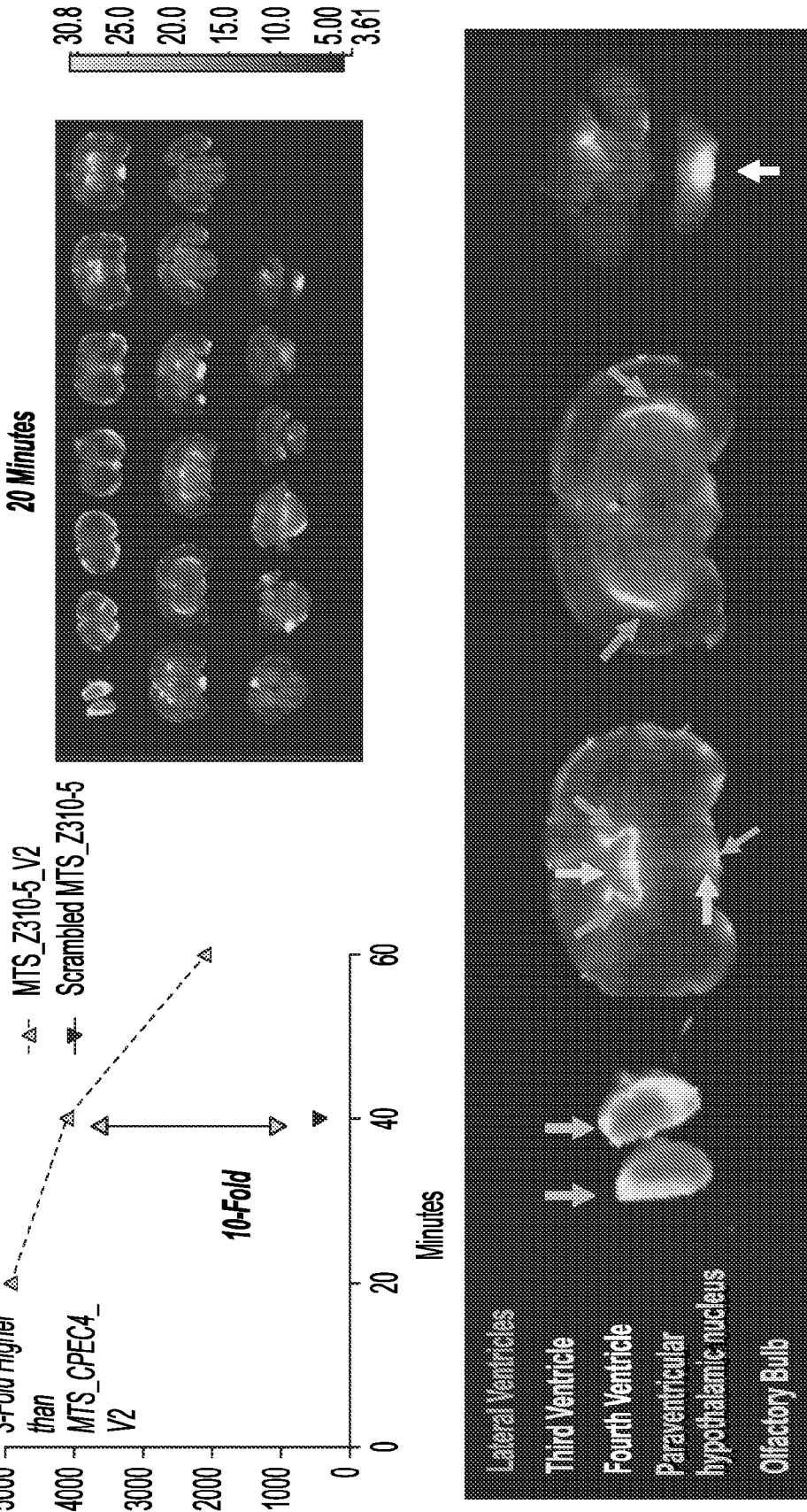
FIG. 26 shows MTS_Z310-5 dimeric peptide enters the CSF and is observed in the ventricular system of the brain. MTS_Z310-5 dimeric peptide comprises two MTS peptides each having the sequence of SKETYSMNAQRQHERS (SEQ ID NO:7).

Dimeric MTS_Z310-5 is present in an amount 3× higher than MTS_CPEC4_V2 (FIG. 26). The MTS is distributed throughout the ventricular system of the brain indicating that the MTS has crossed from the blood stream into the CSF. The MTS is labeled with a dye that allows us to visualize its location. It is injected IV into the tail vein of a rat. After the indicated time, the CSF is isolated from the cisterna *magna*.

Figure 27:
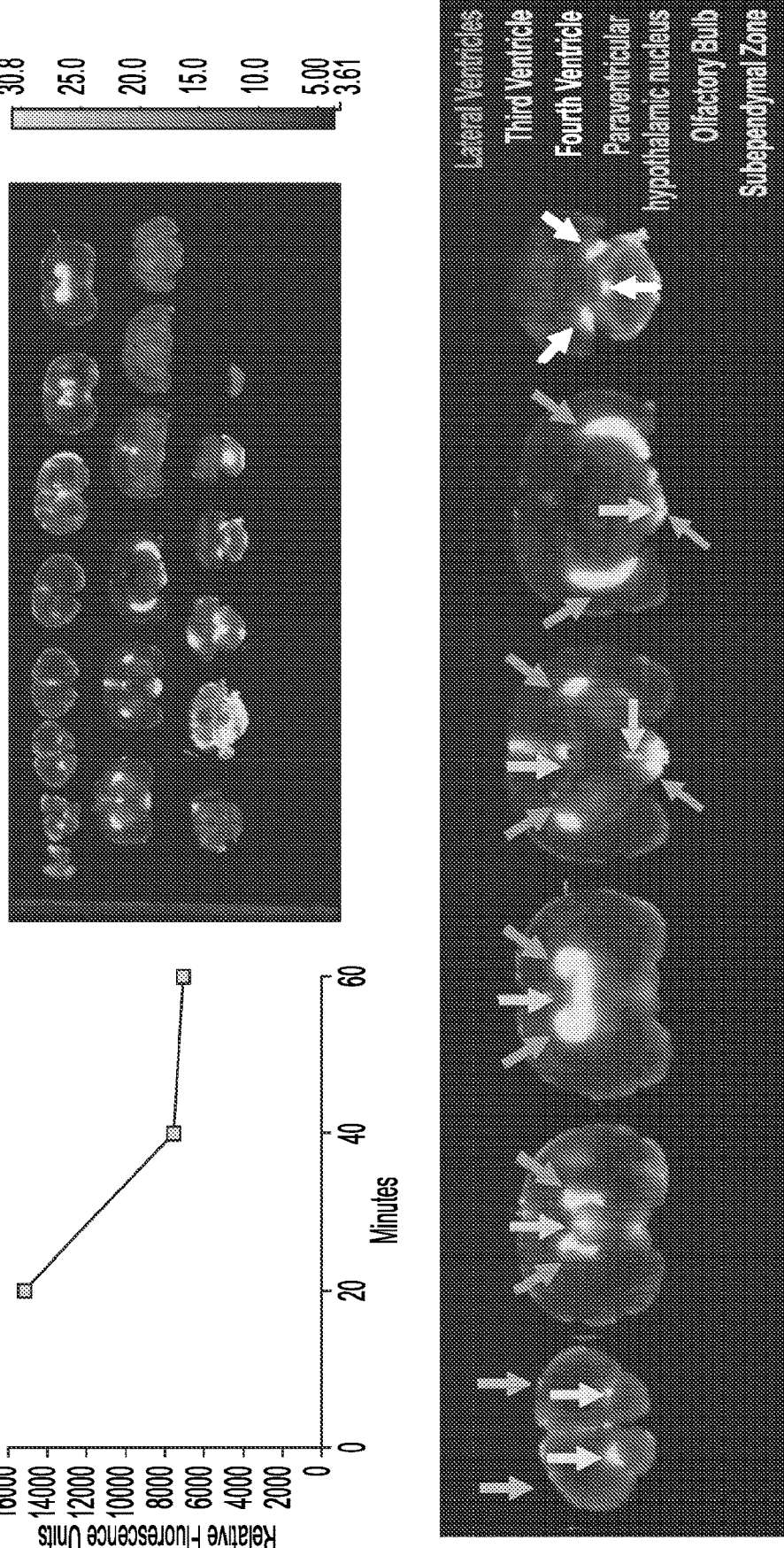
FIG. 27 shows MTS_Z310-2 dimeric peptide enters the CSF and is observed in the ventricular system of the brain. MTS_Z310-2 comprises two MTS peptides each having the sequence of FPSWTSKNQQWTNQRQ (SEQ ID NO:4).

The brain is harvested. After a fixation period, the brain is sliced in 1 mm coronal segments (front to back). The individual slices of the brain are imaged using fluorescence to locate the regions of peptide accumulation Dimeric MTS_Z310-2 is present in an amount 9× higher than MTS_CPEC4_V2 (FIG. 27). The MTS is distributed throughout the ventricular system of then brain indicating that the MTS has crossed from the blood stream into the CSF. The MTS is labeled with a dye that allows us to visualize its location. It is injected IV into the tail vein of a rat. After the indicated time, the CSF is isolated from the cisterna *magna*. The brain is harvested. After a fixation period, the brain is sliced in 1 mm coronal segments (front to back). The individual slices of the brain are imaged using fluorescence to locate the regions of peptide accumulation The chemical conjugation of the dimers and the MTS to the cargo can be seen in FIG. 28. Shown are the general structures of the MTS constructs, particularly monomer and dimer constructs, with different reactive groups or chemical probes on the core.

Those skilled in the art will recognize, or be able to ascertain using no more than routine experimentation, many equivalents to the specific embodiments of the method and compositions described herein. Such equivalents are intended to be encompassed by the following claims.

---

We claim:

1. A molecular transport system (MTS) peptide for use in targeting the central nervous system (CNS), the MTS peptide comprising the amino acid sequence of:

NQEYQHHKIKVRPSHQ (SEQ ID NO:3),
FPSWTSKNQQWTNQRQ (SEQ ID NO:4),
AHMSQKRLPHQVHQHQ (SEQ ID NO:5),
AGNKYEYTMHQKHNK (SEQ ID NO:6),
SKETYSMNAQRQHERS (SEQ ID NO:7),
HRYDADRHHSFTPQYH (SEQ ID NO:8),
NEEMHQAQRHHVQW (SEQ ID NO:9), or
ALEPWGYKQVIKMAPN (SEQ ID NO:10).

2. The MTS peptide of claim 1, wherein the MTS peptide has an N-terminal protection group.

3. The MTS peptide of claim 1, wherein the MTS peptide further comprises a linker.

4. The MTS peptide of claim 3, wherein the linker comprises polyethylene glycol (PEG).

5. The MTS peptide of claim 1, wherein the MTS peptide is covalently conjugated to a cargo, directly or through a linker.

6. The MTS peptide of claim 5, wherein the cargo is a protein, peptide, nucleic acid, antibody, a chemical compound, or a small molecule.

7. The MTS peptide of claim 6, wherein the compound is an imaging agent.

8. The MTS peptide of claim 6, wherein the cargo is a therapeutic.

9. The MTS peptide of claim 5, wherein the MTS peptide further comprises a second MTS peptide, which may be different or the same as the MTS peptide.

10. A composition comprising a MTS peptide of claim 5, wherein the MTS peptide is configured to transport the cargo to the CNS via the cerebral spinal fluid (CSF).

11. The composition of claim 10, wherein the cargo is a protein, peptide, nucleic acid, antibody, a chemical compound, or a small molecule.

12. The composition of claim 11, wherein the compound is an imaging agent.

13. The composition of claim 10, wherein the cargo is a therapeutic.

14. The composition of claim 10, wherein the linker comprises polyethylene glycol (PEG).

* * * * *

SEQUENCE LISTING

```
<160> NUMBER OF SEQ ID NOS: 12

<210> SEQ ID NO 1
<211> LENGTH: 16
<212> TYPE: PRT
<213> ORGANISM: Artificial Sequence
<220> FEATURE:
<223> OTHER INFORMATION: synthetic construct; molecular transport
      peptide

<400> SEQUENCE: 1

Asp Ala Tyr Lys Leu Gln Thr Ser Leu Asp Trp Gln Met Trp Asn Pro
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: synthetic construct; molecular transport
      peptide

<400> SEQUENCE: 2

Asp Gly Tyr Lys Leu Gln Thr Ser Leu Asp Trp Gln Met Trp Asn Pro
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic construct; molecular transport
      peptide

<400> SEQUENCE: 3

Asn Gln Glu Tyr Gln His His Lys Ile Lys Val Arg Pro Ser His Gln
1               5                   10                  15

<210> SEQ ID NO 4
<211> LENGTH: 16
```

```
<212> TYPE: PRT
<213> ORGANISM: Artificial Sequence
<220> FEATURE:
<223> OTHER INFORMATION: synthetic construct; molecular transport
      peptide

<400> SEQUENCE: 4

Phe Pro Ser Trp Thr Ser Lys Asn Gln Gln Trp Thr Asn Gln Arg Gln
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetic construct; molecular transport
      peptide

<400> SEQUENCE: 5

Ala His Met Ser Gln Lys Arg Leu Pro His Gln Val His Gln His Gln
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic construct; molecular transport
      peptide

<400> SEQUENCE: 6

Ala Gly Asn Lys Tyr Glu Tyr Thr Met His Gln Lys His Asn Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: synthetic construct; molecular transport
      peptide

<400> SEQUENCE: 7

Ser Lys Glu Thr Tyr Ser Met Asn Ala Gln Arg Gln His Glu Arg Ser
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: synthetic construct; molecular transport
      peptide

<400> SEQUENCE: 8

His Arg Tyr Asp Ala Asp Arg His His Ser Phe Thr Pro Gln Tyr His
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: synthetic construct; molecular transport
      peptide

<400> SEQUENCE: 9

Asn Glu Glu Met His Gln Ala Gln Arg His His Val Gln Trp
```

-continued

```
1               5                    10

<210> SEQ ID NO 10
<211> LENGTH: 16
<212> TYPE: PRT
<213> ORGANISM: Artificial Sequence
<220> FEATURE:
<223> OTHER INFORMATION: synthetic construct; molecular transport
      peptide

<400> SEQUENCE: 10

Ala Leu Glu Pro Trp Gly Tyr Lys Gln Val Ile Lys Met Ala Pro Asn
1               5                    10              15

<210> SEQ ID NO 11
<211> LENGTH: 12
<212> TYPE: PRT
<213> ORGANISM: Artificial Sequence
<220> FEATURE:
<223> OTHER INFORMATION: synthetic construct; molecular transport
      peptide

<400> SEQUENCE: 11

Tyr Ser Met Asn Ala Gln Arg Gln His Glu Arg Ser
1               5                    10

<210> SEQ ID NO 12
<211> LENGTH: 4
<212> TYPE: PRT
<213> ORGANISM: Artificial Sequence
<220> FEATURE:
<223> OTHER INFORMATION: synthetic construct; molecular transport
      peptide

<400> SEQUENCE: 12

Tyr Ser Met Asn
1
```